United States Patent
Balkwill et al.

(10) Patent No.: US 10,647,766 B2
(45) Date of Patent: May 12, 2020

(54) ANTI-CXCL12 ANTIBODY MOLECULES AND THEIR USES

(71) Applicant: Cancer Research Technology LTD, London (GB)

(72) Inventors: Frances Rosemary Balkwill, London (GB); John McCafferty, Cambridge (GB); Gerard John Graham, Glasgow (GB); Aneesh Karatt Vellatt, Cambridge (GB); Peter Slavny, London (GB)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 134 days.

(21) Appl. No.: 15/535,976

(22) PCT Filed: Dec. 11, 2015

(86) PCT No.: PCT/EP2015/079384
§ 371 (c)(1),
(2) Date: Jun. 14, 2017

(87) PCT Pub. No.: WO2016/096640
PCT Pub. Date: Jun. 23, 2016

(65) Prior Publication Data
US 2017/0362314 A1    Dec. 21, 2017

(30) Foreign Application Priority Data

Dec. 17, 2014  (GB) .................................. 1422502.3

(51) Int. Cl.
*A61K 39/395* (2006.01)
*C07K 16/24* (2006.01)
*A61K 39/00* (2006.01)
*C12N 15/66* (2006.01)

(52) U.S. Cl.
CPC .......... *C07K 16/24* (2013.01); *A61K 39/3955* (2013.01); *A61K 39/00* (2013.01); *A61K 2039/505* (2013.01); *C07K 2317/21* (2013.01); *C07K 2317/24* (2013.01); *C07K 2317/34* (2013.01); *C07K 2317/55* (2013.01); *C07K 2317/56* (2013.01); *C07K 2317/622* (2013.01); *C07K 2317/76* (2013.01); *C07K 2317/92* (2013.01); *C07K 2317/94* (2013.01); *C12N 15/66* (2013.01)

(58) Field of Classification Search
None
See application file for complete search history.

(56) References Cited

U.S. PATENT DOCUMENTS

2010/0158902 A1    6/2010   Pogue et al.

FOREIGN PATENT DOCUMENTS

| WO | 2008/018641 | 2/2008 |
| WO | 2008/021263 | 2/2008 |
| WO | 2008/077945 | 7/2008 |

OTHER PUBLICATIONS

Mallbris et al. (J. Clin. Aesthet. Dermatol. 9(7): 13-15, 2016).*
Schofield et al. Genome Biology 8(11), Article R254, 2007.*
Tamamis, Phanourios, and Floudas, Christodoulos A., (2014) "Elucidating a Key Component of Cancer Metastasis: CXCL12 (SDF-1α) Binding to CXCR4" Journal of Chemical Information and Modeling, 54:1174-1188.
Zhong, et al., (2013) "Development and preclinical characterization of a humanized antibody targeting CXCL12", Clinical Cancer Research, 19:4433-4445.
Chen, et al., (2014) "CXC Chemokine CXCL12 and Its Receptor CXCR4 in Tree Shrews (Tupaia belangeri): Structure. Expression and Function", PLOS ONE, 9(5):1-11, e98231.
Smith, et al., (2014) "Structural Analysis of a Novel Small Molecule Ligand Bound to the CXCL12 Chemokine", Journal of Medicinal Chemistry, 57(22):9693-9699.

* cited by examiner

*Primary Examiner* — Christine J Saoud
(74) *Attorney, Agent, or Firm* — Carol L. Francis; Bozicevic, Field & Francis LLP

(57) ABSTRACT

Anti-CXCL12 antibody molecules and their uses are disclosed, and in particular anti-CXCL12 antibody molecules that are capable of inhibiting a biological activity of CXCL12 in vitro and in vivo and their use for treating CXCL12-mediated disease.

17 Claims, 17 Drawing Sheets
Specification includes a Sequence Listing.

| Antibody | ka (1/Ms) |
|---|---|
| 093_2D06 | ND |
| 114_3H01 | $4.9 \times 10^5$ |

FIG. 3C

| Antibody | ka 1 (1/Ms) | kd 1 (1/s) |
|---|---|---|
| 093_2A02 | $2.0 \times 10^5$ | 0.01 |
| 113_1H12 | $5.1 \times 10^5$ | 0.04 |

FIG. 3D

| kd (1/s) | KD (M) |
|---|---|
| ND | $3.7 \times 10^{-6}$ |
| $5.1 \times 10^{-4}$ | $1.0 \times 10^{-9}$ |

| ka 2 (1/Ms) | kd 2 (1/s) | KD (M) |
|---|---|---|
| 0.007 | $22.2 \times 10^{-4}$ | $16.7 \times 10^{-9}$ |
| 0.015 | $7.9 \times 10^{-4}$ | $3.7 \times 10^{-9}$ |

FIG. 3E

CXCL12 Antibody - 114_3H1

Heavy chain sequence alignment

```
       FW 1                                    CDR 1          FW 2              CDR 2                          FW 3                              CDR 3                FW 4
114_3H1 QVQLVQSGAEVKKPGASVKVSCKVSGYTLTELSMH----WVRQAPGKGLEWMGGFDP----EDGETIYAQKFQGRVTMTEDTSTDTAYMELSSL--GSEDTAVYYCARRVWGSTPNDAF--------DIWGQGTLVTVSS
```

Light chain sequence alignment

```
       FW 1                                    CDR 1          FW 2              CDR 2                          FW 3                              CDR 3                FW 4
114_3H1 DIQMTQSPSSLSASVGDRVTITCRASQ-------SISDYLNWYQQKPGKAPKLLMFAA----SRSQSGVPSRFSGSGS--GTDFTLTISSLQPEDFATYFCQQSYSPP-----------YTFGQGTKVEI---KR
```

CXCL12 Antibody - 113_1H12

Heavy chain sequence alignment

```
       FW 1                                    CDR 1          FW 2              CDR 2                          FW 3                              CDR 3                FW 4
113_1H12 EVQLVQSGAEVKKPGASVKVSCKTSGYTFTNYGIS----WVRQAPGQGLEWMGWISA----YNGNTNYAQKLQGRVTMTTDTSTSTAYMELRSL--RSDDTAVYYCARAGVYYDYFT--------DYWGQGTMVTVSS
```

Light chain sequence alignment

```
       FW 1                                    CDR 1          FW 2              CDR 2                          FW 3                              CDR 3                FW 4
113_1H12 QSELTQPPS-ASGTPGQRVTISCSGSRSN------IGSNSVNWYQQLPGTAPKLLIYNN----DERPSGVPDRFSGSKSG--TSASLAIGGLQSEDEADYYCAAWDDSLNVG-------ELFGGGTKLTV---LG
```

ANTI-CXCL12 ANTIBODY MOLECULES AND THEIR USES

FIELD OF THE INVENTION

The present invention relates to anti-CXCL12 antibody molecules and their uses, and more particularly to anti-CXCL12 antibody molecules that are capable of inhibiting a biological activity of CXCL12 and their use for treating cancer.

BACKGROUND OF THE INVENTION

The C-X-C motif chemokine 12 (CXCL12), also known as stromal cell-derived factor 1 (SDF-1), is a CXC chemokine protein that in humans is encoded by the CXCL12 gene. It is known to bind to two G-protein-coupled receptors, CXCR4 and CXCR7. It participates in many developmental and physiologic processes, including haematopoiesis and angiogenesis. CXCL12 plays a role in angiogenesis by recruiting endothelial progenitor cells (EPCs) from the bone marrow through a CXCR4 dependent mechanism, making it a significant factor in carcinogenesis and neovascularisation linked to tumour progression. Migration another important way in which CXCL12 influences tumour development and progression. CXCL12 also has a role in organ-specific metastasis of several cancers, where cancer cells that express the receptor CXCR4 are attracted to metastasis target tissues that release the ligand, CXCL12. CXCL12 also acts to recruit CXCR4-positive stromal cells and regulates immune cell infiltration. For example, CXCL12 may aid the formation of pre-metastatic niches through the recruitment of regulatory T cells, producing an immunosuppressive environment (Zhao et al, Oncoimmunology, 1(2): 152-161, 2012). In prostate cancer, cancer associated fibroblasts (CAFs) engage monocyte recruitment and M2 polarization through CXCL12 (Comito et al, Oncogene, 33: 2423-2431, 2014). High levels of CXCL12 are associated with low numbers of T cells in a pancreatic cancer model and it was possible to increase T cell infiltration through combined treatment with PD-L1 and CXCR4 inhibitors. This increase in T cell infiltration was accompanied by a significant reduction in tumour volume, highlighting the role of the CXCL12/CXCR4 axis in immune control of cancer (Feig et al, PNAS, 110(50): p20212-20217, 2013).

The CXCL12/CXCR4/CXCR7 pathway has therefore generated considerable interest as a potential therapeutic target given its role in tumour growth, survival and angiogenesis (Balkwill et al., Seminars in Cancer Biology, 14: 171-179, 2004).

WO 2008/018641 (Ono Pharmaceutical Co. Ltd and Medarex, Inc.) discloses human monoclonal antibodies that specifically bind to SDF-1 and proposes their medical uses for treating various B cell malignancies, including breast cancer, multiple myeloma and non-Hodgkin's lymphoma and autoimmune disorders. Zhong et al. (Clinical Cancer Research, 19: 4433-4445, 2013; DOI: 10.1158/1078-0432.CCR-13-0943) discloses a humanised version of a hamster monoclonal antibody 30D8 and shows that it was capable of binding to human and murine CXCL12 in in vitro assays.

SUMMARY OF THE INVENTION

Broadly, the present invention is based on the affinity maturation of anti-CXCL12 antibody molecules and their functional validation in cell-based assays and in vivo to show that the antibody molecules are capable of inhibiting CXCR4-induced cancer cell migration and/or are capable of inhibiting VEGF-induced angiogenesis in vitro. These properties enable the antibody molecules of the present invention to be used in the treatment of cancer, in particular by inhibiting metastasis and or tumour neovascularisation.

Accordingly, in a first aspect, the present invention provides an isolated anti-CXCL12 antibody molecule which specifically binds to human, and optionally murine, CXCL12 and inhibits CXCL12-mediated biological activity, wherein the antibody molecule binds to an epitope of human CXCL12 having the amino acid sequence as set out in SEQ ID NO: 24 that comprises amino acids (a) P10 and R12, and optionally one or more of E15, I28, P32, N45 and/or K54 or (b) P10 and Q48, and optionally one of more of K54 and N45.

In a further aspect, the present invention provides an anti-CXCL12 antibody molecule which comprises: (a) a CDR-H1 having the amino acid sequence of SEQ ID NO: 1, or the amino acid sequence of SEQ ID NO: 1 with one, two, three or more amino acid substitutions, deletions or insertions, (b) a CDR-H2 having the amino acid sequence of SEQ ID NO: 2, or the amino acid sequence of SEQ ID NO: 2 with one, two, three or more amino acid substitutions, deletions or insertions and (c) a CDR-H3 having the amino acid sequence of SEQ ID NO: 3, or the amino acid sequence of SEQ ID NO: 3 with one, two, three or more amino acid substitutions, deletions or insertions; and optionally (d) a CDR-L1 having the amino acid sequence of SEQ ID NO: 4, or the sequences of SEQ ID NO: 4, with one, two, three or more amino acid substitutions, deletions or insertions, (e) a CDR-L2 having the amino acid sequence of SEQ ID NO: 5, or the sequences of SEQ ID NO: 5, with one, two, three or more amino acid substitutions, deletions or insertions and (f) a CDR-L3 having the amino acid sequence of SEQ ID NO: 6, or the sequences of SEQ ID NO: 6, with one, two, three or more amino acid substitutions, deletions or insertions.

In a further aspect, the present invention provides an anti-CXCL12 antibody molecule which comprises (a) a CDR-H1 having the amino acid sequence of SEQ ID NO: 12, or the amino acid sequence of SEQ ID NO: 12 with one, two, three or more amino acid substitutions, deletions or insertions, and (b) a CDR-H2 having the amino acid sequence of SEQ ID NO: 13, or the amino acid sequence of SEQ ID NO: 13 with one, two, three or more amino acid substitutions, deletions or insertions, and (c) a CDR-H3 having the amino acid sequence of SEQ ID NO: 14, or the amino acid sequence of SEQ ID NO: 14 with one, two, three or more amino acid substitutions, deletions or insertions; and optionally (d) a CDR-L1 having the amino acid sequence of SEQ ID NO: 15, or the sequences of SEQ ID NO: 15, with one or more amino acid substitutions, deletions or insertions, and (e) a CDR-L2 having the amino acid sequence of SEQ ID NO: 16, or the sequences of SEQ ID NO: 16, with one, two, three or more amino acid substitutions, deletions or insertions and (f) a CDR-L3 having the amino acid sequence of SEQ ID NO: 17, or the sequences of SEQ ID NO: 17, with one, two, three or more amino acid substitutions, deletions or insertions.

In a further aspect, the present invention provides a pharmaceutical composition comprising an antibody molecule or immunoconjugate as disclosed herein and a pharmaceutically acceptable excipient.

In a further aspect, the present invention provides an antibody molecule or immunoconjugate as disclosed herein for use in a method of treatment of the human or animal body.

In a further aspect, the present invention provides an antibody molecule or immunoconjugate as disclosed herein for use in a method of treatment of a CXCL12-mediated condition.

In a further aspect, the present invention provides the use of an antibody molecule or immunoconjugate as disclosed herein in the manufacture of a medicament for use in treating a CXCL12-mediated condition.

In a further aspect, the present invention provides a method of treating an individual with a CXCL12-mediated condition comprising administering an antibody molecule or immunoconjugate as disclosed herein to an individual in need thereof.

In a further aspect, the present invention provides an antibody molecule of the present invention for use in a method for the diagnosis or prognosis of a patient having a CXCL12-mediated condition. By way of example, the method may comprise determining the presence or amount of CXCL12 in the sample using the antibody and correlating the presence or amount of CXCL12 with the likely outcome of treating the patient with a CXCL12 inhibitor.

In the medical uses and methods of treatment of the present invention, preferably the CXCL12-mediated condition is cancer, including cancer and/or immune cell migration and/or metastasis. The types of cancer that may be treated using the antibodies or immunoconjugates of the present invention include ovarian cancer, breast cancer, bone cancer, prostate cancer, thyroid cancer, pancreatic cancer, multiple myeloma, non-Hodgkin's lymphoma, intraocular lymphoma, follicular centre lymphoma, CML, colorectal cancer, oral squamous carcinoma, cervical cancer, neuroblastoma, kidney cancer, brain cancers, such as glioma and astrocytoma, rhabdmyosarcoma, lung cancer, such as small cell lung cancer, melanoma, B cell malignancies, such as B-cell chronic lymphocytic leukemia (B-CLL), and leukaemia, such as acute myeloid leukaemia (AML) and acute lymphoblastic leukemia. In other embodiments, the present invention may be used for the treatment of WHIM syndrome.

In other uses, the present invention may be used for the treatment of conditions in which CXCL12 signalling is implicated, for example in the mobilisation of cells such as stem cell mobilisation in bone marrow, e.g. in preparation for cell transplantation, similar to the use of a small molecule CXCR4 inhibitor (Plerixafor, AMD3100).

Embodiments of the present invention will now be described by way of example and not limitation with reference to the accompanying figures. However various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

BRIEF DESCRIPTION OF THE FIGURES

FIGS. 3A-3E. Affinity measurement of anti-CXCL12 antibodies using SPR FIGS. 3A, 3B) Sensograms of multiple concentrations of lead and parental anti-CXCL12 Fabs binding to biotinylated CXCL12 immobilised on a streptavidin chip (carboxymethylated dextran matrix pre-immobilised with streptavidin). FIG. 3C) Binding constants of 114_3H1 (labelled as 114_3H01) were determined using 1:1 Langmuir binding model. The equilibrium dissociation constant (KD) of the parent clone 093_2D06 was calculated using steady state binding model due to its very fast off-rate. FIGS. 3D-3E) Antibody 113_1H12 and its parental clone 093_2A02 showed a biphasic binding profile. The binding constants of these antibodies were determined using two-state binding model. Biacore T100 evaluation software was used for all calculations.

FIG. 7. Heavy and light chain sequence alignments of CXCL12 antibodies 114_3H1 and 113_1H12. 114_3H1 Heavy chain sequence corresponds to SEQ ID NO: 7. 114_3H1 Light chain sequence corresponds to SEQ ID NO: 9. 113_1H12 Heavy Chain corresponds to SEQ ID NO: 18. 113_1H12 Light Chain corresponds to SEQ ID NO: 20.

FIG. 8. Sequence alignment of heavy and light chain sequence alignments of CXCL12 antibodies 114 3H1 and 113 1H12 with the antibodies of WO 2008/018641. 114_3H1 Heavy chain sequence corresponds to SEQ ID NO: 7. 114_3H1 Light chain sequence corresponds to SEQ ID NO: 9. 113_1H12 Heavy Chain corresponds to SEQ ID NO: 18. 113_1H12 Light Chain corresponds to SEQ ID NO: 20. 1H2 Heavy chain corresponds to SEQ ID NO: 45. 1H2 Light chain corresponds to SEQ ID NO: 49. 1D3 heavy chain corresponds to SEQ ID NO: 46. 1C6 Heavy chain corresponds to SEQ ID NO: 47. 1C6 Light chain corresponds to SEQ ID NO: 51. 2A5 Heavy chain corresponds to SEQ ID NO: 48. 2A5 Light chain corresponds to SEQ ID NO: 52.

DETAILED DESCRIPTION

Anti-CXCL12 Antibody Molecules

Figure 1:
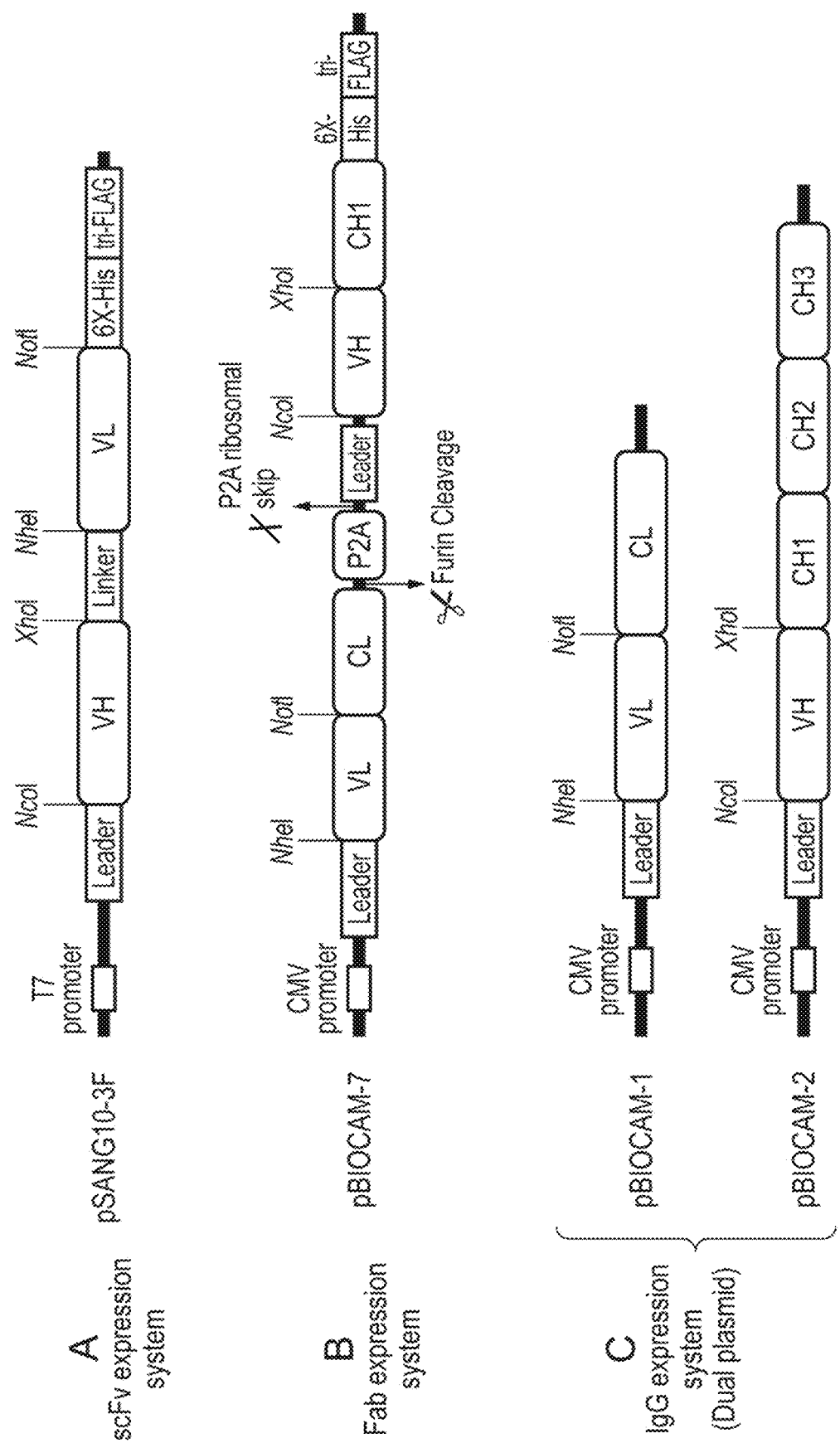
FIG. 1. Vector systems used for expressing anti-CXCL12 antibodies. A) Single chain antibody (scFv) expression using the pSANG10-3F vector. In this plasmid, transcription of the scFv gene is under the control of a bacteriophage T7 promoter. Restriction sites NcoI, XhoI, NheI and NotI facilitate the sub-cloning of variable heavy (VH) and light (VL) chain genes into the Fab and IgG expression vectors. B) Fab antibody expression using the pBIOCAM-7 vector. This plasmid contains a bicistronic Fab expression cassette under the control of a CMV promoter. P2A sequence present between heavy and light chain genes allows the release of antibody heavy polypeptide chain (VH-CH1) downstream of it by a ribosomal skip mechanism. The P2A peptide is post translationally removed from the antibody light chain by Furin cleavage. C) IgG expression using pBIOCAM1-2 dual plasmid system. Heavy (VH-CH1-CH2-Ch3) and light chain expression cassettes are located in two different plasmids. Plasmid pBIOCAM-1 codes for the light chain genes and the pBIOCAM-2 encodes the heavy chain cassette. Transcription of antibody gene is under the control of CMV promoter in both plasmids. Hexa-histidine (6×-His) and tri-FLAG tags fused to the antibody genes in pSANG10-3F and pBIOCAM7 enable purification and immune-detection of the expressed antibodies.

Unless stated otherwise, antibody residues are numbered herein in accordance with the Kabat numbering scheme.

The full length amino acid sequence of CXCL12 is set out as SEQ ID NO: 23 and consists of 89 amino acids. The amino acid sequence of the synthesized 68 amino acid CXCL12 fragment used to select the exemplified antibodies is set out in SEQ ID NO: 24. The epitope mapping studies described in the examples below used a wild type mature CXCL12 polypeptide having the amino acid sequence set out in SEQ ID NO: 25 that include a polyhistidine tag and linker sequence. Preferably, the antibody molecules of the present invention are capable of binding to CXCL12 polypeptides that comprise a polypeptide having at least 90% sequence identity to amino acids 1 to 68 as set out in SEQ ID NO: 23, or a fragment thereof, wherein the fragment is biologically active. Examples of the biological activities of the antibody molecules or immunoconjugates of the present invention include binding to CXCL12, for example to block the interaction of CXCL12 with CXCR4 and optionally also the interaction of CXCL12 with CXCR7. In addition, the biological activities of CXCL12 that may be inhibited (antagonised) by the antibody molecules or immunoconjugates of the present invention include inhibition of VEGF-induced angiogenesis in vitro and/or the inhibition of CXCL12-induced cancer cell migration and/or spreading and/or metastasis. The antibody molecules or immunoconjugates of the present invention may also inhibit the role of CXCL12 in regulating immune cell infiltration. Assays for determining cancer cell migration and metastasis are described in the examples herein.

As described in detail in the examples below, the in vitro affinity maturation of primary anti-CXCL12 antibodies was carried out in two steps. Firstly, the primary antibody sequences were diversified by light chain shuffling to create a derivative library. Secondly, tailored selection and screening procedures were used to identify affinity-improved variants from the light chain shuffled library. The rationale for using light chain shuffling for diversifying primary anti-CXCL12 antibodies was as follows. The original diversity of naïve immune repertoires in vivo (pre-immune B-cell repertoire) or in vitro ("McCafferty library") is derived from the combinatorial rearrangement of germline variable gene segments. A light chain variable region (VL) is encoded by the combination of a long V gene segment and a short joining (J) gene segment. In contrast, the gene encoding heavy chain variable region (VH) is assembled from three gene segments—a V segment, a J segment, and diversity (D) segment and hence is the more diverse of two variable chains. Due to this increased diversity, especially in the CDR3 region, the VH domain tends to play the dominant role in antigen binding and in defining the epitope specificity. As VL domains also make contributions in fine-tuning the binding affinity and antibody expression levels, it is important to have as many VH-VL combinations as possible in a library to identify high affinity antibodies with desirable expression properties. In the examples below, a light chain shuffled library of $2\times10^8$ was created by combining the heavy chain variable regions of 20 anti-CXCL12 antibodies with a repertoire of kappa and lambda light chain variable domains. Thus each original heavy chain was paired with approximately 10 million new light chain partners. Three rounds of phage display selection were carried out under stringent conditions to enrich for high affinity binders from the chain shuffled library. The stringency of the selection conditions was increased at each round by reducing the antigen concentration or using harsher and longer wash steps. Such selection procedures facilitate preferential enrichment of antibody clones with lower dissociation constants.

Affinity maturation selections were carried out in solution-phase, allowing precise control of antigen concentration, which is an important parameter in determining the stringency of a selection. This process identified two antibodies (114_3H1 and 113_1H12) exhibiting the lowest dissociation constants were selected as lead antibodies for detailed characterisation and optimisation. Complete kinetic analysis of 114_3H1 and 113_1H12 and their parent clones (093_2D06 and 093_2A02 respectively) confirmed the improvement in affinity after light chain shuffling. The calculated affinity of 1 nM for 114_3H1 represents a 3800-fold improvement from its parent antibody 093_2D06 (KD=3.8 µM). Since the affinity of the other parent antibody 093_2A02 (KD=16.7 nM) was relatively high at the outset, affinity improvement on its daughter clone 113_1H12 led to a KD=3.7 nM.

In addition to the binding and kinetic studies, the biological properties of the antibody molecules were tested in cell-based functional assays to determine their likely in vivo potency as this does not necessarily correlate with binding, especially if the antibody molecule is intended to modulate complex biological functions. In view of the role of CXCL12 in cancer metastasis and establishing a tumour supportive vasculature, the biological properties of the antibody molecules of the present invention include inhibition of CXCL12-induced cancer cell migration and/or inhibition of VEGF-induced angiogenesis in vitro.

The biological property of inhibiting CXCL12-induced cancer cell migration may be determined using a transwell migration assay used here was a modified version of the Boyden chamber assay used to study the chemotactic response of leukocytes (Boyden, J. Exp. Med. 115, 453-46, 1962) in which migration of fluorescently labelled cancer cells, such as human ovarian cancer cells TOV-21G, seeded in an upper chamber across a porous membrane and into a lower chamber containing CXCL12 is determined.

The biological property of inhibiting angiogenesis may be determined using a cell based assay in which human umbilical vein endothelial cells (HUVECs) and fibroblasts are cultured together in a media containing anti-CXCL12 antibodies and VEGF. The interaction of these two cell types in the presence of VEGF results in the formation of three-dimensional tubes that resemble small capillaries in vivo, see Hetheridge et al. (Biochem. Soc. Trans. 39, 1597-1600, 2011).

The two lead antibodies, 114_3H1 and 113_1H12 were tested using in vitro cancer cell migration assay and angiogenesis assay in order to evaluate their functional characteristics. Both antibodies inhibited CXCL12-induced migration of ovarian cancer cells, with 114_3H1 outperforming 113_1H12. For both antibodies the $IC_{50}$s observed in this assay were comparable to the calculated KD values from SPR analysis. In addition, antibody clone 113_1H12 significantly inhibited VEGF-induced angiogenesis, while antibody clone 114_3H1 partially inhibited VEGF-induced angiogenesis.

Without wishing to be bound by any particular theory, this difference in the properties of the antibodies may be a result of the fact that CXCL12 can induce angiogenesis via interaction with both CXCR4 and CXCR7. Therefore, it may be possible that 114_3H1 only blocks CXCL12/CXCR4 interaction, but not CXCL12/CXCR7 resulting in partial inhibition of angiogenesis. By contrast, 113_1H12 might be blocking CXCL12 binding to both CXCR4 and CXCR7 leading to superior inhibition of CXCL12 induced angiogenesis.

Accordingly, the present invention provides antibody molecules that are based on the antibody clones 113_1H12 or 114_3H1.

In one aspect, the present invention provides an anti-CXCL12 antibody molecule comprising at least one, two, three, four, five, or six of the following CDR sequences based on the CDR sequences of antibody 114_3H1:
  (a) a CDR-H1 having the amino acid sequence of SEQ ID NO: 1, or the amino acid sequence of SEQ ID NO: 1 with one, two, three or more amino acid substitutions, deletions or insertions; and/or
  (b) a CDR-H2 having the amino acid sequence of SEQ ID NO: 2, or the amino acid sequence of SEQ ID NO: 2 with one, two, three or more amino acid substitutions, deletions or insertions; and/or
  (c) a CDR-H3 having the amino acid sequence of SEQ ID NO: 3, or the amino acid sequence of SEQ ID NO: 3 with one, two, three or more amino acid substitutions, deletions or insertions; and/or
  (d) a CDR-L1 having the amino acid sequence of SEQ ID NO: 4, or the sequences of SEQ ID NO: 4, with one, two, three or more amino acid substitutions, deletions or insertions; and/or
  (e) a CDR-L2 having the amino acid sequence of SEQ ID NO: 5, or the sequences of SEQ ID NO: 5, with one, two, three or more amino acid substitutions, deletions or insertions; and/or
  (f) a CDR-L3 having the amino acid sequence of SEQ ID NO: 6, or the sequences of SEQ ID NO: 6, with one, two, three or more amino acid substitutions, deletions or insertions.

In one embodiment, the anti-CXCL12 antibody molecules comprise all six CDRs as defined above optionally with one or more amino acid substitutions, deletions or insertions.

In a further aspect, the present invention provides an anti-CXCL12 antibody molecule comprising at least one, two, three, four, five, or six or more of the following CDR sequences based on the CDR sequences of antibody 113_1E12:
  (a) a CDR-H1 having the amino acid sequence of SEQ ID NO: 12, or the amino acid sequence of SEQ ID NO: 12 with one, two, three or more amino acid substitutions, deletions or insertions; and/or
  (b) a CDR-H2 having the amino acid sequence of SEQ ID NO: 13, or the amino acid sequence of SEQ ID NO: 13 with one, two, three or more amino acid substitutions, deletions or insertions; and/or
  (c) a CDR-H3 having the amino acid sequence of SEQ ID NO: 14, or the amino acid sequence of SEQ ID NO: 14 with one, two, three or more amino acid substitutions, deletions or insertions; and/or
  (d) a CDR-L1 having the amino acid sequence of SEQ ID NO: 15, or the sequences of SEQ ID NO: 15, with one or more amino acid substitutions, deletions or insertions; and/or
  (e) a CDR-L2 having the amino acid sequence of SEQ ID NO: 16, or the sequences of SEQ ID NO: 16, with one, two, three or more amino acid substitutions, deletions or insertions; and/or
  (f) a CDR-L3 having the amino acid sequence of SEQ ID NO: 17, or the sequences of SEQ ID NO: 17, with one, two, three or more amino acid substitutions, deletions or insertions.

In one embodiment, the anti-CXCL12 antibody molecules comprise all six CDRs as defined above (SEQ ID NO: 12-17), optionally with one or more amino acid substitutions, deletions or insertions.

A light chain variable region (VL) is encoded by the combination of a long V gene segment and a short joining (J) gene segment. In contrast, gene encoding heavy chain variable region (VH) is assembled from three gene segments—a V segment, a J segment, and diversity (D) segment and hence is the more diverse of two variable chains. Due to this increased diversity, especially in the CDR3 region, the VH domain tends to play the dominant role in antigen binding and defining the epitope specificity.

Accordingly, in some embodiments, the present invention provides anti-CXCL12 antibody molecules that comprise the CDRs of the heavy chain of the exemplified antibodies as defined herein, optionally each with one, two, three or more amino acid substitutions, deletions or insertions, in combination with light chain derived from a different antibody molecule.

In further aspect, the present invention provides an anti-CXCL12 antibody that comprises (a) a VH domain comprising at least one, at least two, or all three VH CDR sequences selected from (i) CDR-H1 comprising the amino acid sequence of SEQ ID NO: 1, (ii) CDR-H2 comprising the amino acid sequence of SEQ ID NO: 2, and (iii) CDR-H3 comprising an amino acid sequence selected from SEQ ID NO: 3; and (b) a VL domain comprising at least one, at least two, or all three VL CDR sequences selected from (i) CDR-L1 comprising the amino acid sequence of SEQ ID NO: 4, (ii) CDR-L2 comprising the amino acid sequence of SEQ ID NO: 5, and (c) CDR-L3 comprising the amino acid sequence of SEQ ID NO: 6.

In a further aspect, the antibody molecules of the present invention comprise a VH domain comprising the amino acid sequence set out in SEQ ID NO 7, or a sequence having at least 90%, 91%, 92%, 93%, 94%, 95%, 96%, 97%, 98%, 99% or 100% sequence identity to the amino acid sequence of SEQ ID NO: 7. In some embodiments, the VH sequence comprises one or more substitutions, insertions, or deletions relative to the reference sequence, while the antibody molecule retains the property of binding to CXCL12, and optionally one or more of the other biological activities of the anti-CXCL12 antibody molecules of the present invention as described herein. Preferably, the VH domain comprises one, two or three CDRs selected from (i) CDR-H1 comprising the amino acid sequence of SEQ ID NO: 1, (ii) CDR-H2 comprising the amino acid sequence of SEQ ID NO: 2, and (iii) CDR-H3 comprising an amino acid sequence selected from SEQ ID NO: 3.

In a further aspect, the antibody molecules of the present invention comprise a VL domain comprising the amino acid sequence set out in SEQ ID NO 9, or a sequence having at least 90%, 91%, 92%, 93%, 94%, 95%, 96%, 97%, 98%, 99% or 100% sequence identity to amino acid sequence of SEQ ID NO: 9. In some embodiments, the VH sequence comprises one or more substitutions, insertions, or deletions relative to the reference sequence, while the antibody molecule retains the property of binding to CXCL12, and optionally one or more of the other biological activities of the anti-CXCL12 antibody molecules of the present invention as described herein. Preferably, the VL domain comprises one, two or three CDRs selected from (i) CDR-L1 comprising the amino acid sequence of SEQ ID NO: 4, (ii) CDR-L2 comprising the amino acid sequence of SEQ ID NO: 5, and (c) CDR-L3 comprising the amino acid sequence of SEQ ID NO: 6.

In some embodiments, the antibody molecules of the present invention comprise a VH domain comprising the amino acid sequence set out in SEQ ID NO 7, or a sequence having at least 90%, 91%, 92%, 93%, 94%, 95%, 96%, 97%, 98%, 99% or 100% sequence identity to SEQ ID NO: 7, and a VL domain comprising the amino acid sequence set out in SEQ ID NO 9, or a sequence having at least 90%, 91%, 92%, 93%, 94%, 95%, 96%, 97%, 98%, 99% or 100% amino acid sequence identity to SEQ ID NO: 9.

In further aspect, the present invention provides an anti-CXCL12 antibody of the invention comprises (a) a VH domain comprising at least one, at least two, or all three VH CDR sequences selected from (i) CDR-H1 comprising the amino acid sequence of SEQ ID NO: 12, (ii) CDR-H2 comprising the amino acid sequence of SEQ ID NO: 13, and (iii) CDR-H3 comprising an amino acid sequence selected from SEQ ID NO: 14; and (b) a VL domain comprising at least one, at least two, or all three VL CDR sequences selected from (i) CDR-L1 comprising the amino acid sequence of SEQ ID NO: 15, (ii) CDR-L2 comprising the amino acid sequence of SEQ ID NO: 16, and (c) CDR-L3 comprising the amino acid sequence of SEQ ID NO: 17.

In a further aspect, the antibody molecules of the present invention comprise a VH domain comprising the amino acid sequence set out in SEQ ID NO 18, or a sequence having at least 90%, 91%, 92%, 93%, 94%, 95%, 96%, 97%, 98%, 99% or 100% sequence identity to the amino acid sequence of SEQ ID NO: 18. In some embodiments, the VH sequence comprises one or more substitutions, insertions, or deletions relative to the reference sequence, while the antibody molecule retains the property of binding to CXCL12, and optionally one or more of the other biological activities of the anti-CXCL12 antibody molecules of the present invention as described herein. Preferably, the VH domain comprises one, two or three CDRs selected from (i) CDR-H1 comprising the amino acid sequence of SEQ ID NO: 12, (ii) CDR-H2 comprising the amino acid sequence of SEQ ID NO: 13, and (iii) CDR-H3 comprising an amino acid sequence selected from SEQ ID NO: 14.

In a further aspect, the antibody molecules of the present invention comprise a VL domain comprising the amino acid sequence set out in SEQ ID NO 20, or a sequence having at least 90%, 91%, 92%, 93%, 94%, 95%, 96%, 97%, 98%, 99% or 100% sequence identity to amino acid sequence of SEQ ID NO: 20. In some embodiments, the VH sequence comprises one or more substitutions, insertions, or deletions relative to the reference sequence, while the antibody molecule retains the property of binding to CXCL12, and optionally one or more of the other biological activities of the anti-CXCL12 antibody molecules of the present invention as described herein. Preferably, the VL domain comprises one, two or three CDRs selected from (i) CDR-L1 comprising the amino acid sequence of SEQ ID NO: 15, (ii) CDR-L2 comprising the amino acid sequence of SEQ ID NO: 16, and (c) CDR-L3 comprising the amino acid sequence of SEQ ID NO: 17.

In some embodiments, the antibody molecules of the present invention comprise a VH domain comprising the amino acid sequence set out in SEQ ID NO: 18, or a sequence having at least 90%, 91%, 92%, 93%, 94%, 95%, 96%, 97%, 98%, 99% or 100% sequence identity to SEQ ID NO: 18, and a VL domain comprising the amino acid sequence set out in SEQ ID NO: 20, or a sequence having at least 90%, 91%, 92%, 93%, 94%, 95%, 96%, 97%, 98%, 99% or 100% sequence identity to SEQ ID NO: 20.

In a further aspect, the present invention provides anti-CXCL12 antibody molecules capable of binding to an epitope of CXCL12 having the amino acid sequence as set out in SEQ ID NO: 24 or 25 that comprises amino acids (a) P10 and R12, and optionally one or more of E15, I28, P32, N45 and/or K54 or (b) P10 and Q48, optionally one of more of K54 and N45. The exemplified antibody 114_3H1 binds to epitope (a) and antibody 113_1H12 binds to epitope (b).

E15 is outside of regions that involved in receptor or heparin binding. All other epitope residues are within regions involved in receptor binding, which according to numbering of the full length protein at UniProt P48061 (SDF1_HUMAN) are 29-33, 39-41, 48-50, 60-70).

In one aspect, the present invention provides an isolated antibody molecule which binds CXCL12 and which comprises the 114_3H1 VH domain (SEQ ID NO: 7) and/or the 114_3H1 VL domain (SEQ ID NO: 9). Preferably, the CXCL12 is human CXCL12, and optionally also murine CXCL12.

In a further aspect, the present invention provides an isolated antibody which binds CXCL12 and which comprises the 113_1H12 VH domain (SEQ ID NO: 18) and/or the 113_1H12 VL domain (SEQ ID NO: 20). Preferably, the CXCL12 is human CXCL12, and optionally also murine CXCL12.

Generally, a VH domain is paired with a VL domain to provide an antibody antigen binding site, although as discussed further below a VH domain alone may be used to bind antigen. In preferred embodiments, the 114_3H1 or 113_1H12 VH domain (SEQ ID NO: 7 or 18) is paired with the 114_3H1 or 113_1H12 VL domain (SEQ ID NO: 9 or 20), so that an antibody antigen binding site is formed comprising both the 114_3H1 or 113_1H12 VH and VL domains. In other embodiments, the 114_3H1 or 113_1H12 VH is paired with a VL domain other than the 114_3H1 or 113_1H12 VL. Light-chain promiscuity is well established in the art.

One or more CDRs may be taken from the 114_3H1 or 113_1H12 VH or VL domain and incorporated into a suitable framework. This is discussed further below. 114_3H1 VH CDRs H1, H2 and H3 are shown in SEQ ID NOs: 1, 2 and 3, respectively. 114_3H1 VL CDRs L1, L2 and L3 are shown in SEQ ID NOs: 4, 5 and 6, respectively. 113_1H12 VH CDRs H1, H2 and H3 are shown in SEQ ID NOs: 12, 13 and 14, respectively. 113_1H12 VL CDRs L1, L2 and L3 are shown in SEQ ID NOs: 15, 16 and 17, respectively.

In one aspect, the present invention provides an anti-CXCL12 antibody that binds CXCL12 and which comprises:
an antibody VH domain selected from the group consisting of the 114_3H1 VH domain (SEQ ID NO:7) and a VH domain comprising a VH CDR3 with the amino acid sequence of SEQ ID NO: 3 and optionally one or more VH CDR's with an amino acid sequence selected from SEQ ID NO: 1 and SEQ ID NO: 2; and/or
an antibody VL domain selected from the group consisting of the 114_3H1 VL domain (SEQ ID NO: 9) and a VL domain comprising one or more VL CDR's with an amino acid sequence selected from SEQ ID NOs: 4, 5 and 6.

In one aspect, the present invention provides an anti-CXCL12 antibody that binds CXCL12 and which comprises:
an antibody VH domain selected from the group consisting of the 113_1H12 VH domain (SEQ ID NO: 18) and a VH domain comprising a VH CDR3 with the amino acid sequence of SEQ ID NO: 14 and optionally one or more VH CDR's with an amino acid sequence selected from SEQ ID NO: 12 and SEQ ID NO: 13; and/or
an antibody VL domain selected from the group consisting of the 113_1H12 VL domain (SEQ ID NO: 20) and a VL domain comprising one or more VL CDR's with an amino acid sequence selected from SEQ ID NOs: 15, 16 and 17.

As shown in the examples, the antibody molecule of the present invention can tolerate a number of amino acid alterations to the sequences of the CDRs, while retaining the properties of the parent antibody. By way of example, the amino acid sequences of the CDRs of the antibody molecule may each comprise 1, 2, 3, 4, 5, 6, 7, 8, 9 or 10 amino acid substitutions, deletions or insertions as compared to any one of SEQ ID NOs: 1 to 6 and 12 to 17.

Figure 11A:
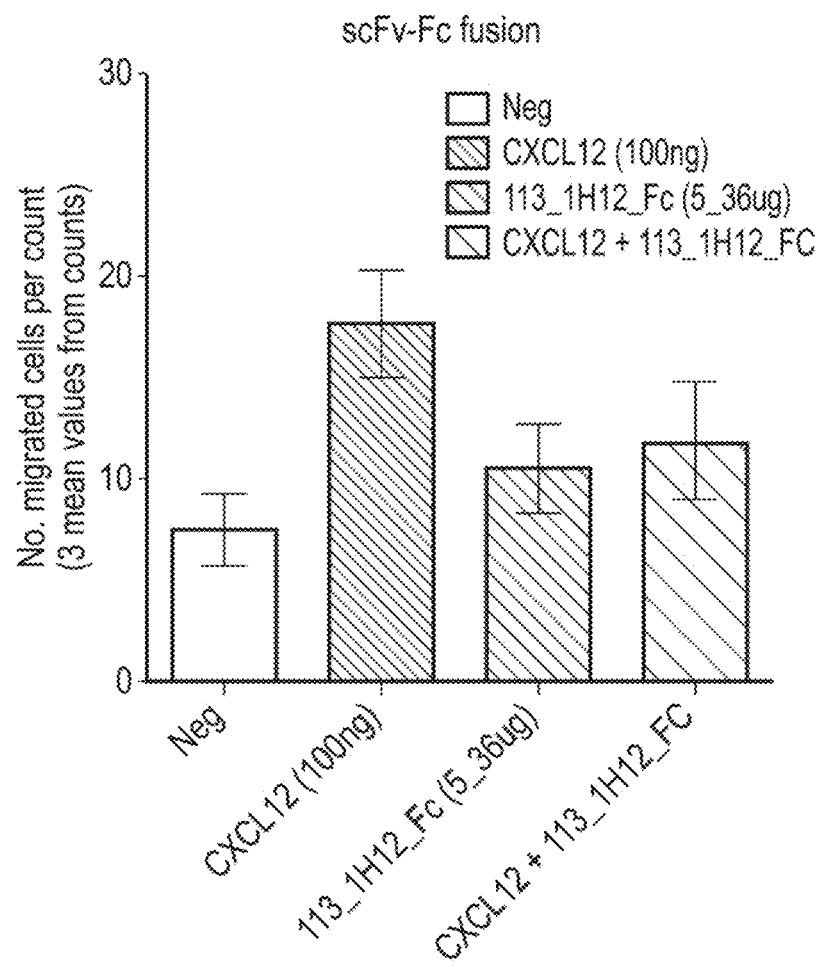
FIGS. 11A-11B. Result of in vitro cell transwell migration assays that show that anti-CXCL12 antibodies of the present invention block migration of TOV21G cancer cells induced by human CXCL12 in scFv-Fc (FIG. 11A) and human IgG2 formats (FIG. 11B).
Figure 11B:
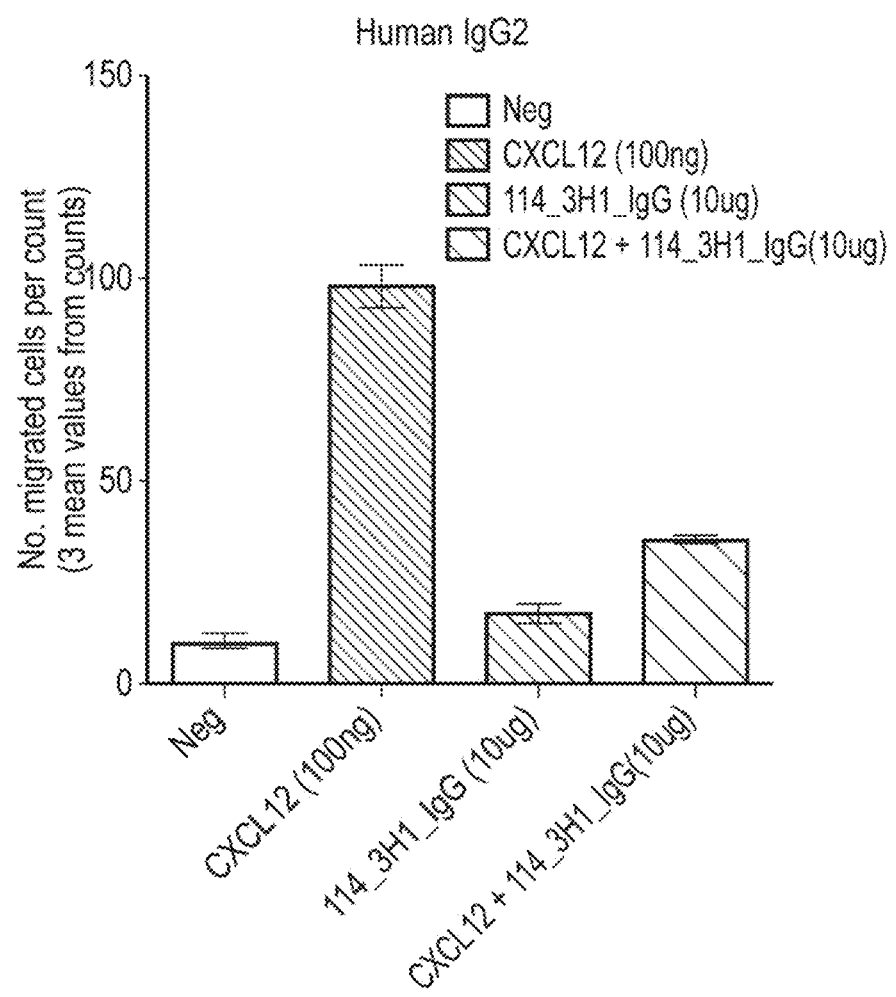

As is well known in the art, the CDRs may be present in a range of different antibody types or framework regions, optionally involving one or more further sequence alterations to ensure retention of a useful property of the antibody as disclosed herein. For example, FIG. 11 shows that the antibodies of the present invention are functional in scFc-Fv fusion and human IgG2 formats.

Each of the VH and VL domains typically comprise three complementarity determining regions (CDRs) responsible for antigen binding, interspersed by framework regions. In one exemplified embodiment, the present invention provides antibody molecules which comprise a VH domain comprising a CDR-H1, CDR-H2 and CDR-H3 having the sequences of SEQ ID NOs: 1, 2 and 3, respectively, and/or a VL domain comprising a CDR-L1, CDR-L2 and CDR-L3 having the sequences of SEQ ID NOs: 4, 5 and 6, respectively. In a further exemplified embodiment, the present invention provides antibody molecules which comprise a VH domain comprising a CDR-H1, CDR-H2 and CDR-H3 having the sequences of SEQ ID NOs: 12, 13 and 14, respectively, and/or a VL domain comprising a CDR-L1, CDR-L2 and CDR-L3 having the sequences of SEQ ID NOs: 15, 16 and 17, respectively.

The present invention also provides an anti-CXCL12 antibody molecule in an scFv format having at least 90%, 91%, 92%, 93%, 94%, 95%, 96%, 97%, 98%, 99% or 100% amino acid sequence identity to SEQ ID NO: 11 or SEQ ID NO: 22.

Generally, the present invention relates to antibody molecules that are capable of inhibiting a biological activity of CXCL12, i.e. antagonist antibody molecules as understood by those skilled in the art. By way of example, the properties may be determined in in vitro cancer cell migration assay and an in vivo angiogenesis assay. Biological activities include inhibiting CXCL12-induced cancer cell growth, inhibiting cancer cell migration, inhibiting cancer cell adhesion, inhibiting cancer metastasis and/or angiogenesis, e.g. VEGF-induced angiogenesis. Optionally, the antibody molecules of the present invention function by binding and sequestering CXCL12 thereby preventing it from interacting with the receptor in the biological system in which it is present.

Binding kinetics and affinity (expressed as the equilibrium dissociation constant Kd) of the anti-CXCL12 antibody molecules may be determined using standard techniques, such as surface plasmon resonance e.g. using BIAcore analysis, for example as described in the experimental examples below. Alternatively, Kd may be measured using a radiolabeled antigen binding assay (RIA) performed with the Fab version of an antibody of interest and CXCL12.

Anti-CXCL12 antibody molecules may have a dissociation constant for CXCL12 of less than 50 nM, less than 40 nM, less than 30 nM, less than 20 nM, less than 10 nM, or less than 1 nM. For example, an antibody molecule may have an affinity for CXCL12 of 1 to 20 nM, e.g. 9 to 15 nM. Preferably, antibody molecules of the present invention have affinity constants ($K_D$) of less than 10 nM, more preferably less than 5 nM and most preferably less than 3 nM for human CXCL12. In addition, the antibodies of the present invention preferably also bind to CXCL12 of other species, such as murine CXCL12, making them compatible with animal models of disease. The affinity constants for binding to CXCL12 can be determined using techniques well known in the art, such as Biacore SPR analysis as exemplified in the experimental examples below.

Anti-CXCL12 antibody molecule of the present invention according to any of the above aspects or embodiments is a monoclonal antibody, including a chimeric, humanized or human antibody. The antibody molecule may be an antibody fragment, e.g., a Fv, Fab, Fab', scFv, scFv-Fc, diabody, or F(ab')$_2$ complete antibody, a triabody, a bispecific antibody or a chimeric antibody.

Preferred formats of antibodies according to the present invention include, IgG, scFv-Fc, Fab and scFv. In another embodiment, the anti-CXCL12 antibody molecule may be a whole antibody. For example, an IgG, IgA, IgE or IgM or any of the isotype sub-classes, particularly IgG1 and IgG4. The anti-CXCL12 antibody molecules may be monoclonal antibodies. Antibody molecules and methods for their construction and use are described, in for example Hollinger & Hudson, Nature Biotechnology 23(9): 1126-1136 (2005).

Antibody molecules normally comprise an antigen binding domain comprising an immunoglobulin heavy chain variable domain (VH) and an immunoglobulin light chain variable domain (VL), although antigen binding domains comprising only a heavy chain variable domain (VH) are also possible (e.g. camelid or shark antibodies). Such antibodies are included within the scope of the present invention.

In some instances, antibody molecules of the present invention may be modified to alter the extent to which the antibody molecule glycosylated. This may be accomplished by altering the amino acid sequence such that one or more of the glycosylation sites present in a parent antibody is created or removed. In particular, where an antibody molecule comprises an Fc region, it is known that alteration of the carbohydrates attached to the Fc region can change the properties of the antibody molecule, in particular by reducing the fucosylation of the Fc region, it is possible to increase ADCC function.

Anti-CXCL12 antibody molecules as described herein may be isolated, in the sense of being free from contaminants, such as antibodies able to bind other polypeptides and/or serum components. Monoclonal antibodies are preferred for most purposes, though polyclonal antibodies may also be employed.

Methods of producing anti-CXCL12 antibody molecules include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80-82). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces. The library may be naive, that is constructed from sequences obtained from an organism which has not been immunised with any of the proteins (or fragments), or may be one constructed using sequences obtained from an organism which has been exposed to the antigen of interest.

In the present invention, the method described in the examples may be employed to screen for further examples of anti-CXCL12 antibodies having antagonistic properties. After production and/or isolation, the biological activity of an anti-CXCL12 antibody molecule may be tested. For example, one or more biological activities may be determined that are selected from inhibiting CXCL12-induced cancer cell growth, inhibiting cancer cell migration, inhibiting cancer cell adhesion, inhibiting cancer metastasis and/or angiogenesis, e.g. VEGF-induced angiogenesis.

Competition between antibody molecules may be assayed easily in vitro, for example using ELISA and/or by tagging a specific reporter molecule to one antibody molecule which can be detected in the presence of one or more other untagged antibody molecules, to enable identification of antibody molecules which bind the same epitope or an overlapping epitope. Such methods are readily known to one of ordinary skill in the art.

The present invention also provides nucleic acid molecules encoding the antibody molecules of the present invention. The nucleic acid molecules are useful for expressing the anti-CXCL12 antibody molecules, for example by incorporating the nucleic acid sequences into an expression vector having control sequences operably linked to the nucleic acid encoding the anti-CXCL12 antibody molecule to control its expression. The vectors may include other sequences such as promoters or enhancers to drive the expression of the inserted nucleic acid, nucleic acid sequences so that the anti-CXCL12 antibody molecule is produced as a fusion and/or nucleic acid encoding secretion signals so that the polypeptide produced in the host cell is secreted from the cell. Suitable vectors can be chosen or constructed, containing appropriate regulatory sequences, including promoter sequences, terminator fragments, polyadenylation sequences, enhancer sequences, marker genes and other sequences as appropriate. Vectors may be plasmids or viral, e.g. 'phage, or phagemid, as appropriate. For further details see, for example, Molecular Cloning: a Laboratory Manual: 2nd edition, Sambrook et al., 1989, Cold Spring Harbour Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Anti-CXCL12 antibody molecules can be obtained by transforming the vectors into host cells in which the vector is functional, culturing the host cells so that the anti-CXCL12 antibody molecule is produced and recovering the anti-CXCL12 antibody molecule from the host cells or the surrounding medium. Prokaryotic and eukaryotic cells are used for this purpose in the art, including strains of *E. coli*, insect cells (e.g. transformed with baculovirus), yeast, and eukaryotic cells such as COS or CHO cells. The choice of host cell can be used to control the properties of the anti-CXCL12 antibody molecule expressed in those cells, e.g. controlling where the polypeptide is deposited in the host cells or affecting properties such as its glycosylation and phosphorylation. If the polypeptide is expressed coupled to an appropriate signal leader peptide it may be secreted from the cell into the culture medium. Following production by expression, the antibody molecule of the present invention may be isolated and/or purified from the host cell and/or culture medium, as the case may be, and subsequently used as desired, e.g. in the formulation of a composition which may include one or more additional components such as a carrier as described elsewhere in the present application.

Accordingly, in further aspects, the present invention provides nucleic acid encoding an anti-CXCL12 antibody molecule of the present invention, an expression vector comprising the nucleic acid encoding an anti-CXCL12 antibody molecule, operably linked to control sequences to direct its expression, and host cells transformed with this expression vector. In a still further aspect, the present invention provides a method of producing an anti-CXCL12 antibody molecule of the present invention, the method comprising culturing the host cells and isolating the anti-CXCL12 antibody molecule thus produced.

Derivatised Antibody Molecules

The antibody molecules of the present invention may also be derivatised to modify their properties, and in particular their pharmacological properties, such as half-life (e.g. increasing half-life). An example is the conjugation of antibody molecules to poly(alkylene glycol) molecules, in particular polyethylene glycol (PEG) molecules, that may be used to enhance the half-life or other pharmacological properties of polypeptide therapeutics. Pegylation is a known strategy for modifying the properties of therapeutic polypeptides, such as peptides, proteins and antibodies. In general, the attachment of PEG molecules to polypeptides is used to alter their conformation, electrostatic or hydrophobic properties, and lead to improvements in their biological and pharmacological properties, such as increasing drug solubility, reducing dosage frequency, modulating (especially increasing) circulating half-life, increasing drug stability and increasing resistance to proteolytic degradation Pegylation works by increasing the molecular weight of the therapeutic polypeptide by conjugating the polypeptide to one or more PEG polymer molecules. This is particularly applicable to types of antibody molecules that are fragments of complete antibodies, such as Fab fragments.

This may be carried out to the antibody molecules of the present invention by reacting suitable functional groups present in the antibody molecules with a reactive poly (alkylene glycol) molecules. Depending on the functional groups available in the antibody molecules of the present invention, it may be possible to pegylate the antibody molecules in a selective way, for example by identifying suitable reactive cysteine residues in the antibody molecules. Poly(alkylene glycol) molecules are interchangeably referred to in the art as poly(alkylene oxide) molecules and are polyethers. Poly(alkylene glycol) molecules may have linear, branched, comb or star structures and generally are highly water soluble. In addition, the basic poly(alkylene glycol) structure may be provided with one or more reactive functional groups such as hydroxy, amine, carboxylic acid, alkyl halide or thiol groups to facilitate the reaction of the poly(alkylene glycol) molecule with other species such as polypeptides. Preferred poly(alkylene glycol) molecules include those substituted at one or more hydroxyl positions with a chemical group, such as an alkyl group having between one and four carbon atoms. Preferred poly(alkylene glycol) molecules for use in accordance with the present invention are polyethylene glycol ("PEG") molecules, although the skilled person would be able to derivatise antibody molecules of the present invention using other poly(alkylene glycol) molecules, such as polypropylene glycol or polyethylene-polypropylene glycol copolymers. Poly(alkylene glycol) molecules, including PEGs, typically have molecular weights between about 400 Da and about 80 kDa, more preferably between about 1 kDa and about 60 kDa, and more preferably between about 5 kDa and about 50 kDa, e.g. molecular weights of 10 kDa, 20 kDa, 30 kDa or 40 kDa. Poly(alkylene glycol) molecules that may be used in accordance with the present invention are well known in the art and publicly available, for example from commercially available sources such as SigmaAldrich.

The present invention also provides immunoconjugates comprising an anti-CXCL12 antibody molecule as described herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one aspect, an immunoconjugate of the present invention is an antibody-drug conjugate (ADC) in which an antibody is conjugated to one or more drugs, for example a chemotherapeutic drug. The antibody moiety is optionally linked to the drug via a linker.

Imaging Applications

The antibody molecules of the present invention may additionally be labelled to enable them to be employed for imaging, either in conjunction with or independent of their therapeutic uses. Techniques for labelling antibodies are well known in the art that enable the antibodies to be used in a range of imaging and spectroscopic applications. This might be useful in a number of different medical or research applications, for example in the fields of oncology, cardiovascular medicine or graft rejection.

One particular example of the use of the antibody molecules for imaging involves the use of radionuclide labels in nuclear medicine imaging techniques, such as Single Photon Emission Computed Tomography (SPECT), an imaging technique that detects gamma rays emitted from a radionuclide to produce a two dimensional image of the distribution of the radionuclide in a sample or subject, and Positron Emission Tomography (PET), an imaging technique that three-dimensional images by detecting pairs of gamma rays emitted indirectly by a positron-emitting radionuclide introduced into a sample or subject. Antibody molecules having radionuclide labels may also be employed for multi-modal studies in which imaging techniques are combined, either by selecting radionuclides that are active in more than one imaging technique or by labelling the antibody molecules with more than one type of label.

The antibody molecules of the present invention may be labelled with a radionuclide, for example a radionuclide provided as a complex, or conjugated to a second molecule, such as a linker, that is can be associated with the label. Examples of radionuclides for use in imaging techniques or therapy include technetium, rhenium, copper, cobalt, gallium and indium isotopes such as Tc-99m, Re-186, Re-188, Co-57, Ga-67, In-111 (SPECT), Cu-64, Cu-60, Cu-61, Cu-62, Cu-67, Tc-94m, Ga-68, Co-55 (PET). In general, technetium isotopes are employed for imaging purposes, rhenium isotopes for therapeutic purposes and copper isotopes for both imaging and therapy.

Medical Uses

CXCL12 has been reported to be involved in angiogenesis by recruiting endothelial progenitor cells (EPCs) from the bone marrow through a CXCR4 dependent mechanism, making it an significant factor in carcinogenesis and neovascularisation linked to tumour progression. CXCL12 also has a role in tumour metastasis where cancer cells that express the receptor CXCR4 are attracted to metastasis target tissues that release the ligand, CXCL12. The CXCL12/CXCR4/CXCR7 pathway has therefore generated considerable interest as a potential therapeutic target given its role in tumour growth, survival and angiogenesis.

Accordingly, CXCL12 has been shown to be important in the organ-specific metastasis of tumours, as reviewed in Balkwill et al., Seminars in Cancer Biology, 14: 171-179, 2004. Tumours that express CXCL12/CXCR4 include ovarian cancer, breast cancer, bone cancer, prostate cancer, thyroid cancer, pancreatic cancer, multiple myeloma, non-Hodgkin's lymphoma, intraocular lymphoma, follicular center lymphoma, CML, colorectal cancer, oral squamous carcinoma, cervical cancer, neuroblastoma, kidney cancer, brain cancers such as glioma and astrocytoma, rhabdmyosarcoma, lung cancer, such as small cell lung cancer, melanoma, B cell malignancies, such as B-cell chronic lymphocytic leukemia (B-CLL), and leukaemias, such as acute myeloid leukaemia (AML).

CAFs are known to secrete CXCL12 and this increases angiogenesis and tumour growth directly in breast cancer (Orimo et al., Stromal fibroblasts present in invasive human breast carcinomas promote tumor growth and angiogenesis through elevated SDF-1/CXCL12 secretion, Cell, 121(3): 335-348, 2005) and pancreatic cancer (Feig et al., Targeting CXCL12 from FAP-expressing carcinoma associated fibroblasts synergizes with anti-PD-L1 immunotherapy in pancreatic cancer. P.N.A.S., 110: 50: 20212-20217, 2013). In addition high levels of CXCL12 are associated with low numbers of T cells in a pancreatic cancer model and it was possible to increase T cell infiltration through combined treatment with PD-L1 and CXCR4 inhibitors. This increase in T cell infiltration was accompanied by a significant reduction in tumour volume, highlighting the role of the CXCL12/CXCR4 axis in immune control of cancer (Feig et al, PNAS, 110(50): p20212-20217, 2013).

Certain chemotherapeutics, anti-angiogenic agents and irradiation have been shown to cause additional upregulation of CXCL12/CXCR4, which aids tumour recurrence post-treatment. An increased level of CXCL12 triggers mobilisation of endothelial progenitors (Shaked et al, Cancer Cell, 14(3): 263-273, 2008) and the recruitment of monocytes to the tumour (Hughes et al, Cancer Res, 75(17): OF1-OF13, 2015), which stimulate tumour invasion, neovascularisation and metastasis as well as suppress anti-tumour immune responses. Therefore, the combination of the anti-CXCL12 antibodies of the present invention with these type of CXCL12/CXCR4-inducing agents could be of clinical benefit.

In other embodiments, the antibody molecules or immunoconjugates of the present invention may be used in the treatment of WHIM Syndrome (Warts, Hypogammaglobulinemia, Infections, and Myelokathexis syndrome) is a rare congenital immunodeficiency disorder characterized by chronic noncyclic neutropenia which results from mutations in the chemokine receptor CXCR4.

In some embodiments, the antibody molecules or immunoconjugates of the present invention may be administered in conjunction with a further cancer therapy or in conjunction with radiotherapy. By way of example, the antibody molecules or immunoconjugates of the present invention may be administered in conjunction with a chemotherapeutic agent, an antibody therapy, immune modulatory therapy, surgery or in conjunction with radiotherapy, or in conjunction with cell mediated therapy. In some embodiments, the antibody molecule and the further cancer therapy are administered together, optionally as a combined formulation. Alternatively, the antibody molecule and the further cancer therapy may be administered by alternation, with either the further cancer therapy administered before the antibody molecule, or the further cancer therapy administered after the antibody molecule. The combination may be administered in accordance with clinical practice, for example being administered at intervals from about one week to three weeks.

In one particular embodiment, the antibody molecules of the present invention are administered in conjunction with an angiogenesis inhibitor. Based on the mode of action of the antibody molecules of the present invention, combination therapies with angiogenesis inhibitors might provide additive or synergistic effects (see Liang et al., CXCR4/CXCL12 axis promotes VEGF-mediated tumor angiogenesis through Akt signaling pathway, Biochem. Biophys. Res. Commun. 359(3): 716-722, 2007).

Angiogenesis inhibitors as used herein include agents that inhibit angiogenesis, vasculogenesis, or undesirable vascular permeability, either directly or indirectly. It should be understood that the angiogenesis inhibitors include those agents that bind and block the angiogenic activity of the angiogenic factor or its receptor. See, e.g., Grothey and Galanis (2009) Nat. Rev. Clin. Oncol. 6(9): 507-18 (e.g. Table 1 lists large-molecule VEGF inhibitors), Ivy, Wick and Kaufman (2009) Nat. Rev. Olin. Oncol. 6(9): 569-7 (e.g. Supplementary Table 1 lists small molecule receptor tyrosine kinase inhibitors).

Angiogenesis inhibitors include antibodies or peptide-antibody fusions targeted to angiogenesis-promoting growth factor receptors, e.g. Bevacizumab (Avastin®), Cetuximab (Erbitux®), Ramucirumab (Cyramza®), Icrucumab, HuMV833, 2C3, Aflibercept (Zaltrap®) and IMC-1C11. Other angiogenesis inhibitors include small molecule kinase inhibitors, e.g. Sorafenib (Nexavar®), Sunitinib (Sutent®), Pazopanib (Votrient®), Everolimus (Afinitor®), AEE788, AAL881, AAL993, ZD4190, ABT-869 (Linifanib), PTK787 (Vatalanib), AMG706 (Motesanib), Cediranib (Recentin), Axitinib (Inlyta®), Vandetanib (Caprelsa®), SU6668, ZD1839, Telatinib, Nintedanib (Vargatef®), Brivanib alaninate, BMS-605541, BMS-645737, CEP-7055, Dovitinib, CP-547,632, E7080, GW654652, KRN633, Tivozanib, OSI-930, PD173074, PF-00337210, SU1498, Semaxanib (SU5416), SU5614, SU11657, SU14813, TKI-28, TKI-31 and ZM323881. Examples of native angiogenesis inhibitors are endostatin and angiostatin. Other drugs used to inhibit angiogenesis include thalidomide, squalamine and angiozyme.

Bevacizumab (Avastin®) is a recombinant humanised anti-VEGF monoclonal antibody generated according to Presta et al. (1997) *Cancer Res.* 57(20):4593-4599. Afibercept is a recombinant peptide-antibody fusion consisting of VEGF-binding portions fused to the Fc portion of human IgG1. Sorafenib (Nexavar®) is a multikinase inhibitor that blocks the receptor tyrosine kinases VEGFR, PDGFR (Platelet Derived Growth Factor Receptor), RAF serine/threonine kinases and c-KIT. In chemical terms, sorafenib is named 4-[4-[[4-chloro-3-(trifluoromethyl) phenyl]carbamoylamino]phenoxy]-N-methyl-pyridine-2-carboxamide and has the structure:

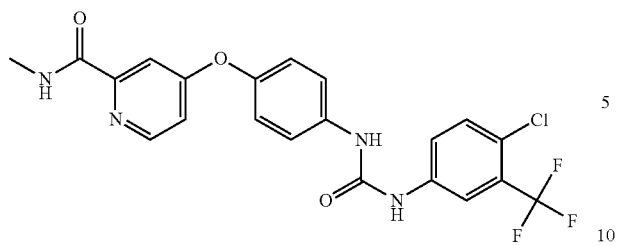

Sunitinib (SUTENT®) is a small molecule multi-targeted receptor tyrosine kinase inhibitor used in the treatment of cancer. It inhibits cellular signalling by targeting PDGFR and VEGFR. In chemical terms sunitinib is named N-(2-diethylaminoethyl)-5-[(Z)-(5-fluoro-2-oxo-1H-indol-3-ylidene)mWethyl]-2,4-dimethyl-1Hpyrrole-3-carboxamide and has the structure:

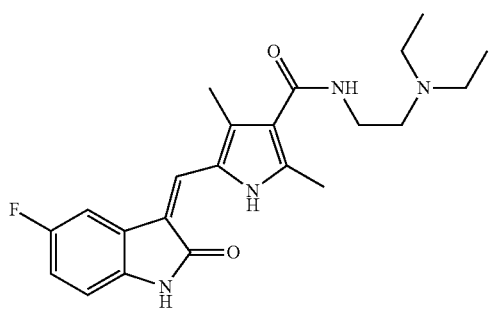 [SMILES: CCN(CC)CCNC(=O)c1c(C)[nH]c(/C=C2\C(=O)Nc3ccc(F)cc32)c1C]

Pazopanib (VOTRIENT®) is a multikinase inhibitor used in the treatment of cancer. It is known to target c-KIT, PDGFR and VEGFR. In chemical terms it is named 5-[[4-[(2,3-Dimethyl-2Hindazol-6-yl)methylamino]-2-pyrimidinyl]amino]-2-methylbenzolsulfonamide and has the structure:

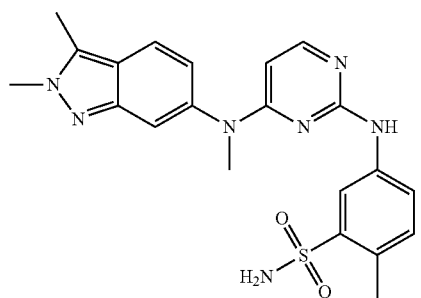 [SMILES: Cc1ccc(Nc2nccc(N(C)c3ccc4c(C)n(C)nc4c3)n2)cc1S(N)(=O)=O]

Everolimus (AFINITOR®) is a signal transduction inhibitor targeting mTOR (mammalian target of rapamycin). In chemical terms it is named dihydroxy-12-[(2R)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.O hexatriaconta-16,24,26,28-tetraene-2,3,10,14,20-pentone and has the structure:

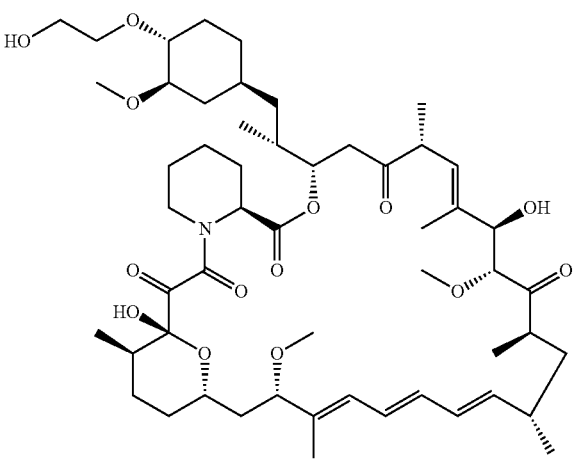 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

AEE788 is a small molecule drug being evaluated for treatment for cancer. It is a combined inhibitor of both the EGFR (epidermal growth factor receptor) and VEGFR family members. In chemical terms it is named 6-[4-[(4-Ethyl-piperazin-1-yl)methyl]phenyl]-N-[(1R)-1-phenylethyl]-7H-pyrrolo[2,3-d]pyrimidin-4-amine and has the structure:

PTK787 (VATALANIB) is a protein kinase inhibitor that inhibits angiogenesis being developed for cancer treatment. It inhibits VEGF receptors, PDGFR-beta and c-kit. In chemical terms it is named N-(4-chlorophenyl)-4-(pyridin-4-ylmethyl)phthalazin-1-amine and has the structure:

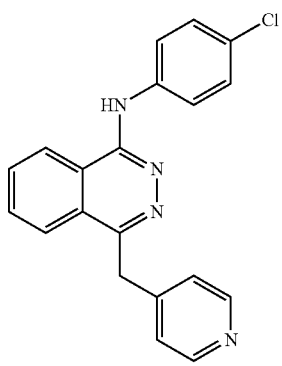 [SMILES: Clc1ccc(Nc2nnc(Cc3ccncc3)c3ccccc23)cc1]

Examples of additional chemotherapeutic agents include an EGFR pathway inhibitor, such as an anti-EGFR antibody or an EGFR kinase inhibitor, such as cetuximab, panitumumab, Iressa (gefitinib or (N-(3-chloro-4-fluoro-phenyl)-7-methoxy-5 6-(3-morpholin-4-ylpropoxy)quinazolin-4- amine), or Tarceva (erlitonib or N-(3-ethynylphenyl)-6,7-bis (2-methoxyethoxy) quinazolin-4-amine), or other agents such as HERCEPTIN™ (trastuzumab). Further examples of chemotherapeutic agents include alkylating agents, such as cisplatin, carboplatin and 10 oxaliplatin, anthracyclines, plant alkaloids such as taxanes and vinca alkaloids, and topoisomerase inhibitors such as irinotecan, topotecan, amsacrine, etoposide, etoposide phosphate and teniposide, or fluorouracil (5FU).

In a further possibility, the antibody molecules of the present invention may be administered with an immune therapeutic, for example an immune pathway agent, small molecule agent or an antibody specific for PD-1, PDL-1, CTLA-4 or OX40.

In a further possibility, the antibody molecules of the present invention may be antibody-drug conjugates in which the antibody molecule is linked to a drug or toxin. This may be done to direct the drug or toxin to a target site in a biological system where CXCL12 is present. This approach may entail engineering the antibody molecule to provide a functional group capable of reacting with the drug or toxin, or alternatively providing the antibody molecule with a linker group that is capable of reacting with the drug or toxin. In this aspect of the present invention, the drug may also be a pro-drug for conversion to active drug at a target site in a patient.

Accordingly, the present invention provides an immunoconjugate which comprises an antibody molecule of the present invention conjugated to a cytotoxic moiety or an immunostimmulatory moiety. By way of illustration, the cytotoxic moiety may be an alkylating agent, an alkaloid, a platinum coordination complex, a cytotoxic peptide, a radioactive agent, or a pro-drug capable of conversion into a cytotoxic moiety.

In a further aspect, the present invention relates to antibody molecules for use in a method of diagnosis or prognosis of a condition in which CXCL12 is implicated. In some embodiments, the antibody molecules of the present invention may be used in assays for identifying patients who are likely to be more responsive to treatment than a wider class of patients considered as a whole. This in turn may enable therapy, for example using antibody molecules of the present invention, to be directed to those patients most likely to respond, while providing the patients for whom treatment is less likely to be successful with alternative forms of therapy. On related aspect, the present invention provide a method of assaying for the presence of CXCL12 in a sample, the method comprising contacting the sample with antibody molecules of the present invention so that the CXCL12 binds to the antibody molecules to form a complex and detecting the complex thus produced. Alternatively or additionally, the methods may also employ antibody molecules of the present invention as reagents for detecting the binding of CXCL12 to a capture antibody. Preferably, the method comprises determining the presence or amount of CXCL12 in the sample using the antibody and correlating the presence or amount of CXCL12 with the likely outcome of treating the patient with a CXCL12 inhibitor.

In this case, the antibody molecules may be used in an ELISA-type format or otherwise labelled linked to a detectable molecule such as, but not limited to, radioactive or fluorescent labels or to enzymes which utilise a chromogenic substrate. Examples of radiolabels of use in this technique are $^{32}P$, $^{3}H$ or $^{14}C$. Examples of fluorescent molecules of use in this technique are green fluorescent protein, Fluorescein IsoThioCyanate (FITC), Rhodamine IsoThioCyanate (TRICT) Cy3 and Cy5 Dyes. Examples of enzymes with chromagenic substrates of possible use in this technique are peroxidase, alkaline phosphatase or glucose oxidase.

Preferably, the method of the present invention is an in vitro method carried out on a sample obtained from said individual. In some embodiments of the present invention, the method may therefore comprise an initial step of obtaining a sample from the individual in question and/or preparing the sample for analysis. Preferred examples of samples for use in the method include blood samples, tissue samples or cell samples.

Additional variations of the above techniques exist that will be apparent to someone skilled in the art.

Pharmaceutical Compositions

The anti-CXCL12 antibody molecules or immunoconjugates of the present invention may be comprised in pharmaceutical compositions with a pharmaceutically acceptable excipient. A pharmaceutically acceptable excipient may be a compound or a combination of compounds entering into a pharmaceutical composition which does not provoke secondary reactions and which allows, for example, facilitation of the administration of the anti-CXCL12 antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-CXCL12 antibody molecule.

In some embodiments, anti-CXCL12 antibody molecules or immunoconjugates may be provided in a lyophilised form for reconstitution prior to administration. For example, lyophilised antibody molecules may be re-constituted in sterile water and mixed with saline prior to administration to an individual.

Anti-CXCL12 antibody molecules will usually be administered in the form of a pharmaceutical composition, which may comprise at least one component in addition to the antibody molecule. Thus pharmaceutical compositions may comprise, in addition to the anti-CXCL12 antibody molecule, a pharmaceutically acceptable excipient, carrier, buffer, stabilizer or other materials well known to those skilled in the art. Such materials should be non-toxic and should not interfere with the efficacy of the anti-CXCL12 antibody molecule. The precise nature of the carrier or other material will depend on the route of administration, which may be by bolus, infusion, injection or any other suitable route, as discussed below.

For intra-venous administration, e.g. by injection, the pharmaceutical composition comprising the anti-CXCL12 antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

A pharmaceutical composition comprising an anti-CXCL12 antibody molecule may be administered alone or in combination with other treatments, either simultaneously or sequentially dependent upon the condition to be treated.

An anti-CXCL12 antibody molecule as described herein may be used in a method of treatment of the human or animal body, including prophylactic treatment (e.g. treatment before the onset of a condition in an individual to reduce the risk of the condition occurring in the individual; delay its onset; or reduce its severity after onset). The method of treatment may comprise administering an anti-CXCL12 antibody molecule to an individual in need thereof.

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc., is within the responsibility of general practitioners and other medical doctors and may depend on the severity of the symptoms and/or progression of a disease being treated. Appropriate doses of antibody molecules are well known in the art (Ledermann J. A. et al. (1991) Int. J. Cancer 47: 659-664; Bagshawe K. D. et al. (1991) Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of an antibody molecule may be determined by comparing its in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 μg to 1 g for systemic applications, and 1 μg to 1 mg for topical applications. An initial higher loading dose, followed by one or more lower doses, may be administered. Typically, the antibody will be a whole antibody, e.g. the IgG1, IgG2, IgG3 or IgG4 isotype, according to differences in amino acid sequence in the hinge and Fc regions. These different isotypes affect the in vivo half-lives of the antibody molecules and their ability to induce effector functions. Hence, the choice of IgG isotype may be used to engineer the in vivo properties of the antibody molecules of the present invention. For neutralising soluble antigens such as CXCL12, effector functions are less critical and so the use of an antibody isotype lacking effector function (such as IgG2) may be preferred to determine the benefits of CXCL12 neutralisation without interference of the host immune system.

This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intra-venous administration. Treatment may be periodic, and the period between administrations is about two weeks or more, e.g. about three weeks or more, about four weeks or more, or about once a month. Treatment may be given before, and/or after surgery, and/or may be administered or applied directly at the anatomical site of surgical treatment or invasive procedure. Suitable formulations and routes of administration are described above.

In some preferred embodiments, the therapeutic effect of the anti-CXCL12 antibody molecule may persist for several half-lives, depending on the dose. For example, the therapeutic effect of a single dose of anti-CXCL12 antibody molecule may persist in an individual for 1 month or more, 2 months or more, 3 months or more, 4 months or more, 5 months or more, or 6 months or more.

Material and Methods
Generation CXCL12 Neutralising Antibodies by Phage Display Technology
Panning Antibody Libraries on CXCL12

The 'McCafferty naïve antibody library', which contains more than 10 billion antibody clones in scFv format, was used for isolating anti-CXCL12 antibodies and the resulting antibodies were then screened in a cell-based assay to assess potential to block the CXCL12-CXCR4 interaction. In more detail, two rounds of panning were carried out on biotinylated CXCL12 immobilised on streptavidin or neutravidin. In order to avoid enriching for antibody clones that bind to streptavidin or neutravidin two strategies were employed. Round 1 panning was carried out on biotinylated CXCL12 immobilised on streptavidin using the phage library that has been depleted of any streptavidin binders (known as 'de-selection; or 'subtractive selection'). For Round 2, neutravidin was used (instead of streptavidin) to immobilise CXCL12. Polyclonal phage prepared from round 2 panning output was tested in a TRF binding assay against CXCL12, streptavidin, neutravidin and a non-specific antigen (NCK1) to confirm specific enrichment. The binding signal observed was specific to CXCL12 and no detectable binding was observed for streptavidin, neutravidin and NCK1.

Anti-CXCL12 Antibody Screening

The scFv population from the Round 2 panning output was PCR amplified and cloned into the pSANG10-3F expression vector and transformed into BL21. The psANG10-3F encodes a hexa-histidine tag (for Ni-affinity purification) and tri-FLAG tag (for detection) downstream of the scFv gene. 940 individual transformants were picked into 10×96 well culture plates and antibody expression was induced using auto-induction media. Recombinant monoclonal antibodies secreted into culture supernatant after overnight induction were tested for binding to CXCL12. The culture supernatants containing secreted scFvs were used for a TRF binding assay in which scFv binding to biotinylated-CXCL12 (immobilised on streptavidin in 96 well plates) was detected using an anti-FLAG antibody conjugated to europium. Clones with signal above 1000 FU (100 fold above background) were considered as positive for CXCL12 binding.

Approximately 24% (224/940) of the clones screened were found be positive for CXCL12 binding. The top 184 clones were cherry-picked for sequence analysis and further characterisation. Sequences of cherry-picked clones were generated by Sanger sequencing using 4 primers and a consensus sequence was assembled for each clone. CDR and framework regions of the consensus sequences were analysed using BLAZE antibody analysis software. By focusing the analysis on variation in CDR3 of heavy and light chains, 118 unique scFv sequences were found. With in these sequences there were additional changes in other CDRs or framework residues bringing 38 more unique sequences, i.e. 156 unique sequences from 184 sequenced. Detailed analysis of the framework regions revealed a preference for certain heavy chain and light chain germline families. Vh3 (62%) and Vh1 (43%) are the most frequently found heavy chain families while Vκ1 (58%) followed by Vκ2 (17%) dominate the light chain sequences.

streptavidin-PE prior to binding detection by flow cytometry. The two-step detection method gave a sharp fluorescent peak in comparison to the broad distribution of fluorescence observed with one-step detection method. In addition, the pre-complexing of CXCL12 and streptavidin-PE would result in tetrameric presentation of CXCL12 molecules. This would result in avidity effects which could hinder the blocking of CXCL12-MOLT-4 cell interaction by monomeric scFvs. For these reasons, the two-step method for detection of CXCL12 binding was chosen for the blocking assay. A dose response analysis identified the optimum concentration of CXCL12 for the assay as 7.5 µg/ml.

A two-fold dilution series of biotinylated CXCL12 starting from 40 µg/ml was incubated with MOLT-4 cells expressing CXCR4. The CXCL12 binding to the cells

TABLE 1

A snapshot of sequence analysis of the primary CXCL12 antibodies. The framework and the CDR regions were analysed using BLAZE software and the antibodies were clustered based on similarity in VH and VL CDR3 sequence (for example, 093_E11 and 093_E10).

| Clone ID | VH germline | VL germline | VH CDR3 | VL CDR3 |
| --- | --- | --- | --- | --- |
| 093_1C03 | Vh1_DP-5_(1-24) | Vlambda3_3h | LISGSYRLEDYF . . . DH (SEQ ID NO: 26) | QAWDSSTG . . . YV (SEQ ID NO: 35) |
| 093_2G07 | Vh3_DP-86_(3-66) | Vk1_DPK1_(O18.O8) | EASDPRYYYDSSGYYYGM . . . DV (SEQ ID NO: 28) | QQYDNLP . . . LT (SEQ ID NO: 36) |
| 093_2A11 | Vh3_DP-42_(3-53) | Vk1_DPK4_(A20) | EASDPRYYYDSSGYYYGM . . . DV (SEQ ID NO: 28) | QKYNSAP . . . RT (SEQ ID NO: 37) |
| 093_2H09 | Vh1_DP-88_(1-e) | Vk2_DPK18_(A17) | DYNDWGAF . . . EL (SEQ ID NO: 28) | VQGTHWP . . . WT (SEQ ID NO: 38) |
| 093_1H10 | Vh1_DP-5_(1-24) | Vk1_DPK4_(A20) | EGYDSSGYGARPRYYYYGM . . . DV (SEQ ID NO: 29) | QQSYNTP . . . RT (SEQ ID NO: 39) |
| X093_1E11.093_1E10 | Vh3_DP-53_(3-74) | Vk2_DPK18_(A17) | DSLDGNGSGSWDDAF . . . DI (SEQ ID NO: 53) | VQGTHWP . . . WT (SEQ ID NO: 40) |
| 093_2G12 | Vh1_DP-5_(1-24) | Vlambda6_6a | GSAYYYGSGSYYKAPYYYYYGMDV (SEQ ID NO: 31) | QSYDSSN . . . QV (SEQ ID NO: 41) |
| 093_2B01 | Vh3_DP-46_(3-30.3) | Vk1_DPK1_(O18.O8) | GMGYGM . . . DL (SEQ ID NO: 32) | QQYDNLP . . . YT (SEQ ID NO: 42) |
| 093_2F10 | Vh3_DP-47_(3-23) | Vlambda2_DPL10_(2b2) | EGGDPTTPTTT . . . TV (SEQ ID NO: 33) | CSYAGPFT . . . VI (SEQ ID NO: 43) |
| 093_2F12 | XVh3_DP-49_(3-30.5) | Vlambda1_DPL3_(1g) | DDSTADL . . . DY (SEQ ID NO: 34) | AAWDDSLSGP . . . YV (SEQ ID NO: 44) |

Identification of Antibodies that Block CXCL12 Binding to CXCR4

A large panel of unique CXCL12 binders were identified from the primary screening and sequence analysis. In order to identify antibodies that block CXCL12-CXCR4 interaction, a cell based CXCL12-CXCR4 binding assay using flow cytometry was established. A human acute lymphoblastic leukemia cell line (MOLT-4) was identified as an ideal CXCR4 expressing cell line for CXCL12-CXCR4 binding assay as they were found to be negative for CXCR7 expression. In this assay, the binding of biotinylated-CXCL12 to CXCR4 expressing MOLT-4 cells was detected using streptavidin conjugated with phycoerythrin (streptavidin-PE). Anti-CXCL12 antibodies were then tested for their ability to inhibit this interaction.

At first, a number of pilot experiments were carried out to identify optimum assay parameters (such as detection method, amount of CXCL12, concentration of the blocking agent etc.) in order to achieve the maximum assay sensitivity. A one-step binding detection method was tested and compared to a two-step binding detection method. The one step binding detection method involved direct staining of MOLT-4 cells with biotinylated-CXCL12 that has been pre-complexed with streptavidin-PE and detecting the binding by flow cytometry. In contrast, the two-step binding detection method involved incubation of MOLT-4 cells with biotinylated CXCL12, washing, and then staining with binding was detected by streptavidin-PE using flow cytometry. The mean fluorescence observed for each test sample was plotted against the CXCL12 concentration.

39 clones from the 118 anti-CXCL12 antibodies identified from primary screening for blocking were selected for this assay on the basis of heavy chain CDR3 sequence diversity and binding signal in the primary screen. ScFV antibody was produced from these clones and was purified by immobilised metal ion affinity chromatography. The purified antibodies (and a non-specific antibody) were then tested for blocking activity in CXCL12-MOLT-4 cell binding assay. Based on the percentage inhibition of CXCL12-MOLT-4 cell binding, 20 antibodies with blocking activity greater than 45% were selected for further study (Table 2).

TABLE 2

Top 20 blocking antibodies from the cell-based CXCL12-CXCR4 binding assay.

| Rank | Clone ID | Percentage blocking in cell-binding assay |
| --- | --- | --- |
| 1 | 093_1C03 | 99 |
| 2 | 093_2A02 | 96 |
| 3 | 093_2D06 | 94 |
| 4 | 093_1F01 | 87 |
| 5 | 093_2G07 | 86 |
| 6 | 093_2G10 | 83 |

TABLE 2-continued

Top 20 blocking antibodies from the cell-based CXCL12-CXCR4 binding assay.

| Rank | Clone ID | Percentage blocking in cell-binding assay |
|---|---|---|
| 7 | 093_1C04 | 65 |
| 8 | 093_2C02 | 64 |
| 9 | 093_2E04 | 63 |
| 10 | 093_1A10 | 63 |
| 11 | 093_1A08 | 59 |
| 12 | 093_1G07 | 58 |
| 13 | 093_2G09 | 57 |
| 14 | 093_1A09 | 54 |
| 15 | 093_1F09 | 54 |
| 16 | 093_1G10 | 51 |
| 17 | 093_2E12 | 51 |
| 18 | 093_2D05 | 51 |
| 19 | 093_2A10 | 46 |
| 20 | 093_1A11 | 45 |

Affinity Maturation and Functional Characterisation of Primary Anti-CXCL12 Antibodies Primary antibody phage display selections and screening identified several antibodies that block CXCL12 binding to CXCR4. Therapeutic applications often require monoclonal antibodies with affinities in the low-to-sub-nanomolar range to accomplish the desired clinical efficacy. Panning from the "McCafferty library" under low stringency conditions generally yields primary antibodies with affinity ranging from 10 nM-1 µM. Such antibodies are often affinity matured in vitro to attain sufficient affinity for the given application.

In vitro affinity maturation of antibodies can be achieved by mimicking the in vivo process that occurs during a humoral immune response. The initial response to antigen stimulation involves the selection of antigen specific B-cells from a large and diverse pre-immune repertoire of B-cells expressing low affinity antibodies. These primary, low affinity antibodies then undergo a process called somatic hypermutation in which they accumulate point mutations in the heavy and light variable regions. The B-cells expressing high affinity antibodies compete with B-cells expressing low affinity antibodies for antigen stimulation to survive and proliferate. By repeated cycles of somatic hypermutation and preferential expansion of B-cells expressing higher affinity antibodies, the immune system gradually establishes an effective response to invading pathogens. Similar to the in vivo process, commonly used in vitro affinity maturation strategies involve two key steps, diversification of the primary antibody sequence and the selective enrichment of affinity improved antibodies using a selection platform such as phage display technology. Diversification of primary antibody sequence can be done by introducing mutations to the variable regions using random or targeted mutagenesis. Alternatively, new combinations of heavy and light variable regions can be made by recombining selected heavy or light chains with a repertoire of partner chains by a process known as chain shuffling.

Given the modular nature of antibodies, chain shuffled libraries can be easily created by simple cloning hence this was the chosen method for affinity maturing primary anti-CXCL12 antibodies. Since the heavy chain variable domains commonly play the dominant role in antigen binding and defining the epitope specificity, light chain shuffling is preferred over heavy chain shuffling to preserve the binding epitope of the primary antibodies.

Construction of Chain Shuffled Libraries and Stringent Phage Display Selections on CXCL12

In order to create a light chain shuffled library, the antibody heavy chain regions from the top 20 blocking antibodies were amplified by PCR. The resultant PCR products were cloned into a phage display light chain library preparation encompassing a repertoire of naïve lambda and kappa light chain variable region partners (in vector pSANG4). The ensuing plasmid population was transformed into E. coli TG1 to yield a library containing $2.6 \times 10^8$ scFv clones. Thus each original heavy chain was paired with approximately 10 million new light chain partners. In order to assess the frequency of heavy chain insertion, 20 random clones from the light chain shuffled library were analysed by colony PCR screen. 19 out of 20 clones showed the presence of a full-length scFv gene (not shown) suggesting that approximately 95% of clones in the library are light chain shuffled recombinants.

Successful isolation of high affinity antibodies from any library requires stringent selection conditions that can selectively enrich high affinity binders. Antibodies with high affinities can be enriched by iterative rounds of phage selection using diminishing antigen concentrations. This method relies on the competition for limiting amounts of antigen and the preferential enrichment of variants with lower dissociation constants. For precise control of antigen concentration, phage display selections are carried out in solution phase. The phage antibodies are allowed to bind to a biotinylated antigen in solution and the bound phage is subsequently captured using a streptavidin-coated surface for washing and elution. The stringency of the selection can be further increased at this step by including a number of harsh and long washing steps.

For the isolation of high affinity anti-CXCL12 antibodies from the light chain shuffled library, three rounds of solution phase selections were carried out on biotinylated CXCL12. The optimum antigen concentration for each round was determined empirically by selecting the phage antibodies against a range of antigen concentrations and comparing the output numbers with a "no antigen" control. The third round also included a set of selections in which the captured phage-antigen complex was subjected to 17-hour wash (washed 6 times every hour with phosphate buffered saline containing 0.2% Tween-20) to further increase the stringency.

Screening the Selection Outputs for Affinity Matured Monoclonal Binders

The scFv populations from round 3 selection outputs were PCR amplified and cloned into the pSANG10-3F expression vector and the resulting plasmid DNA was transformed into E. coli BL21 DE3 cells. 960 individual transformants were picked into 10×96 well culture plates and the antibody expression was induced using auto-induction media. Recombinant monoclonal antibodies secreted into the culture supernatant after overnight induction, were screened for their ability to bind CXCL12 in a TRF binding assay. 48% (458/960) of the clones screened from various selection outputs were found to be positive for CXCL12 binding. The binding signals exhibited by these clones were significantly better than those of the clones isolated from the naïve library. 37% of the clones screened from the chain shuffled selection outputs showed binding signal above 10,000 fluorescent units (FU). In contrast, only 12% of the clones isolated from the naïve library exhibited binding signals exceeding 10,000 FU. Since clones tested in the screen were not normalised for expression, the observed improvement in the CXCL12 binding could be due to improved expression or improved affinity.

The CXCL12 binding clones were and analysed using BLAZE antibody sequence analysis software. Analysis of the heavy and light chain CDR3 diversity identified 227 unique clones. Although 20 different VH genes were used in the construction of the chain shuffled library, only 9 VH genes were represented amongst the 227 unique clones identified. Within this set there were four major clone families. These were derived from the VH gene of primary clones 093_2A02 (122/227), 093_2D06 (38/227), 093_2G07 (24/227) and 093_2A10 (22/227). Similar to the clones isolated from the naïve library, VL germline usages of these chain shuffled clones were dominated by Vκ1 (63%) and Vκ2 (22%) germline families.

The CXCL12 binding signal observed for a particular clone in the primary screen was dependent on the combined effect of antibody expression and affinity. Since the antibody expression varies significantly from clone-to-clone, ranking antibodies by their binding signal in the primary screen do not necessarily correlate with their affinities. Therefore, an expression-independent secondary screening assay was used to identify high affinity anti-CXCL12 antibodies with superior binding kinetics. In this screening assay, dissociation constants (off-rates) of the top 150 anti-CXCL12 scFv antibodies were analysed using surface plasmon resonance (SPR). The dissociation constant of an antibody-antigen interaction is concentration independent and therefore a normalisation for differential antibody expression was not required. However, due to the tendency of scFv antibodies to dimerise in solution, the accurate measurement of monovalent antibody-antigen (1:1) interactions is complicated and often results in erroneous determination of binding constants. Hence a panel of 24 antibodies showing low dissociation constants in the scFv-SPR screen were reformatted as Fab antibodies for another cycle of 'off-rate screen'. Unlike scFvs, Fab antibodies are stable in monomeric format and are optimal for accurate kinetic analysis. Antibody clones, 114_3H1 (derived from 093_2D06) and 113_1H12 (derived from 093_2A02) showed the best off-rates (i.e. the lowest dissociation constants) amongst the 24 Fab antibodies tested. These two clones were selected as lead anti-CXCL12 antibodies for detailed characterisation. The sequences of these antibodies are provided in the sequence listing.

Expression and Purification of Anti-CXCL12 Antibodies as Fabs and IgGs in Mammalian Cells All antibody work up to the second cycle of off-rate screen was performed with antibodies in scFv format. ScFv format is well suited for phage display selections and subsequent screening of large number clones to identify a panel of lead antibodies due to the efficient expression in E. coli. However, there are a number of limitations associated with this format that make it sub-optimal for downstream biophysical and biological characterisation. For example, affinity determination of scFvs is complicated due to their propensity to dimerise in solution. Poor stability of scFv molecules makes them susceptible to aggregation and precipitation thereby limiting their long-term storage. In addition, the presence of high level of endotoxin in scFv preparations from E. coli, restricts their usage in number of cell based assays. Hence, scFvs identified from primary screening assays are usually reformatted to larger and more stable antibody formats and are expressed in mammalian cells for downstream characterisation and in vivo testing. The two lead anti-CXCL12 antibodies and their parent clones were reformatted to Fabs and IgGs. Fabs are optimal for accurate determination of the binding constants. Whilst the IgG is the preferred format for majority of clinically approved antibodies and the antibodies in development. Their superior in vivo half-life, and the ability to engage the host immune system are ideal for the treatment of diseases, such as cancer. In addition, the bivalent nature of an IgG molecule greatly enhances its antigen neutralisation capability both in vitro and in vivo.

The sequences of the anti-CXCL12 antibodies of the present invention could be used in any appropriate expression systems designed for the generation of antibody molecules. All scFv antibodies discussed in this work were expressed from the pSANG10-3F vector, in which a single T7 promoter drives the expression of heavy and light variable domains that are connected by a glycine-serine linker (FIG. 1A). In this system, the scFv gene is transcribed as a single mRNA and translated as a single protein. In contrast, commonly used mammalian Fab and IgG expression systems use expression cassettes that transcribe and translate heavy and light chain genes separately. Here we used a bicistronic vector (pBIOCAM-7) for transient expression of anti-CXCL12 Fabs in HEK-293 cells (FIG. 1B). In pBIOCAM7 antibody light (VL+CL) and heavy chain (VH+CH) genes are separated by a gene segment that encodes a "ribosome skipping" peptide from porcine teschovirus-1 (known as the P2A peptide). This Fab expression system produces a single mRNA transcript for the whole Fab cassette (VL+CL-P2A-VH+CH). However, during translation the ribosome skips the synthesis of the glycyl-prolyl peptide bond at the C-terminus of P2A peptide resulting in the release of the polypeptide chain immediately downstream of it. The heavy and light chain polypeptides are then folded and assembled independently in the endoplasmic reticulum (ER) to form Fab molecules. The furin cleavage site at the C-terminus of light chain facilitates the posttranslational removal of the P2A peptide from the Fab protein.

For the expression of anti-CXCL12 antibodies in IgG format, a dual plasmid system was used in which the heavy and light chain expression cassettes were carried on two different plasmids (FIG. 1C). Upon co-transfection of these plasmids into HEK-293 cells, heavy and light chain genes are transcribed and translated separately before being assembled into IgG molecules in ER. IgG antibodies are divided into 4 isotypes (IgG1, IgG2, IgG3 and IgG4) according to differences in amino acid sequence in the hinge and Fc regions. These different isotypes affect the in vivo half-lives of the antibody molecules and their ability to induce effector functions. Hence, the choice of IgG isotype may be used to engineer the in vivo properties of the antibody molecules of the present invention. For neutralising soluble antigens such as CXCL12, effector functions are less critical. In fact, it is desirable to have antibodies lacking effector functions for future in vivo experiments in order to determine the benefits of CXCL12 neutralisation without interference of the host immune system. Therefore, we chose IgG2 Isotype, which exhibits reduced antibody dependent cell-mediated cytotoxicity (ADCC) and complement dependent cytotoxicity (CDC).

For Fab and IgG expression, the variable regions of the lead antibodies (114_3H1 and 113_1H12) and their parent clones (093_2D06 and 093_2A02) were sub-cloned into the pBIOCAM-7 vector and IgG2 expression plasmids (pBIOCAM-1 and pBIOCAM2-IgG2).

Figure 2:
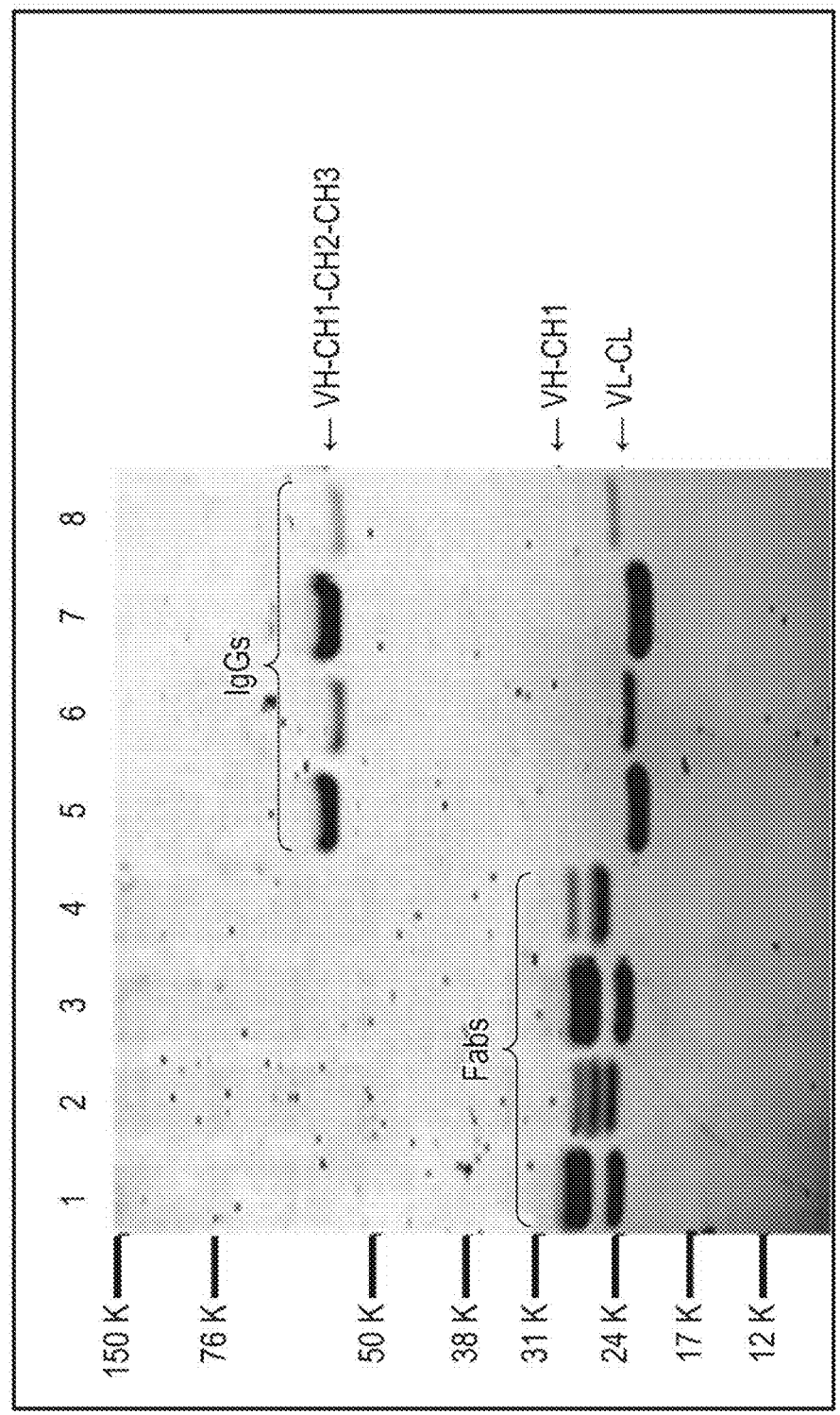
FIG. 2. SDS-PAGE analysis of anti-CXCL12 Fabs and IgGs. Lead anti-CXCL12 antibodies and their parent clones were expressed in HEK-293 cells as Fabs and IgGs. Affinity purified antibodies were visualised on a reducing SDS-PAGE gel using SYPRO® Red staining. Clones 093_2D06, 093_2A02, 114_3H1 (labelled as 114_3H01) and 113_1H12 were loaded respectively as Fabs (lanes 1-4) and IgGs (lanes 5-8). Smearing of VH-CH1 bands in some of the Fab preparations could be due to the cleavage of the FLAG tag (which often occurs in Flag tagged proteins).

Transfection quality DNA was prepared for these plasmids and transfected into HEK-293F cells for transient antibody expression. Fab and IgG antibodies were purified from the cell culture supernatants (6 days post transfection) using Nickel and Protein-G affinity chromatography methods respectively. As illustrated in FIG. 2, purified Fabs and IgGs were composed of a heavy and a light chain domains of the expected sizes.

Affinity Measurement of Anti-CXCL12 Antibodies

Figure 3A:
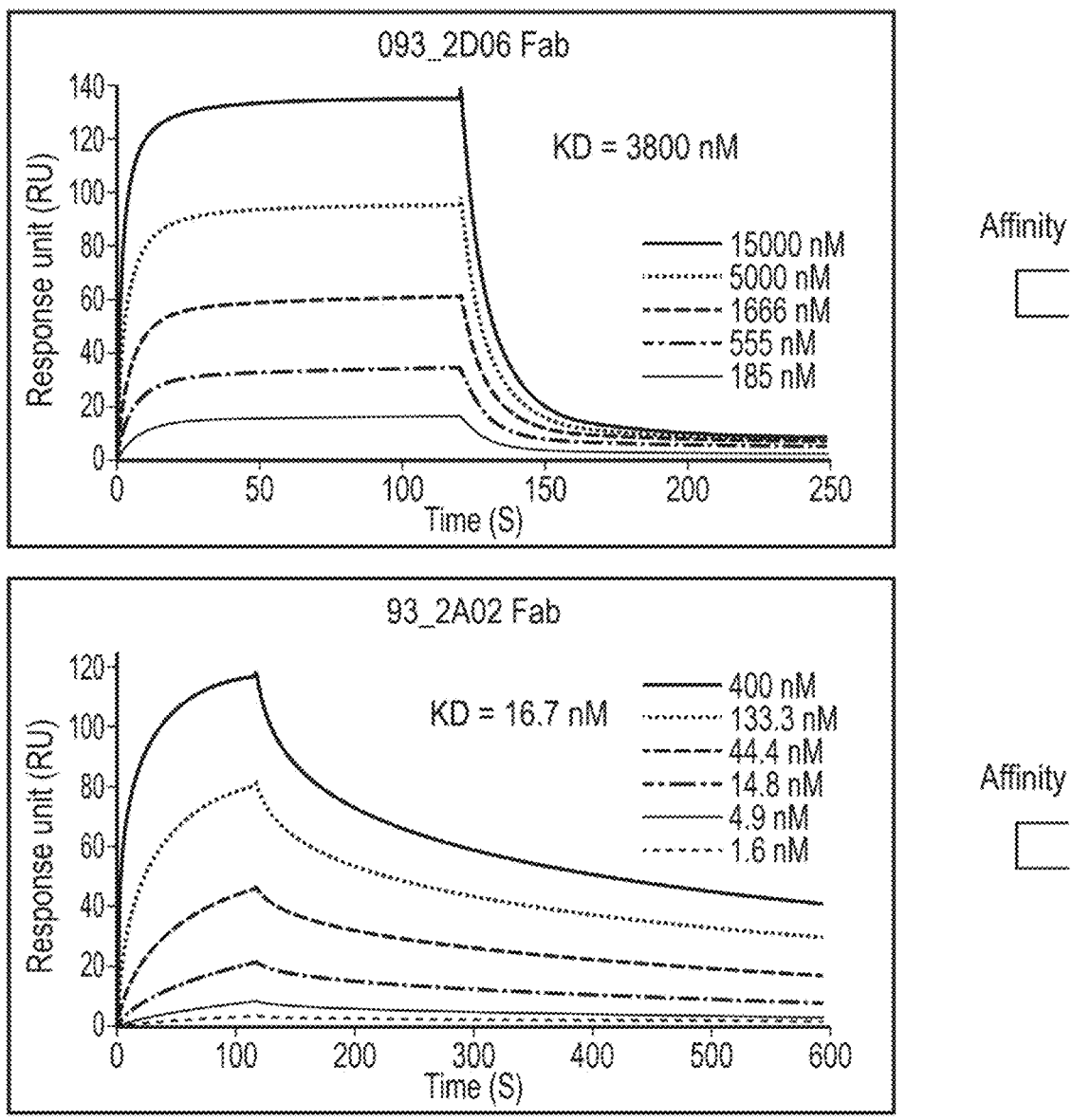
Figure 3B:
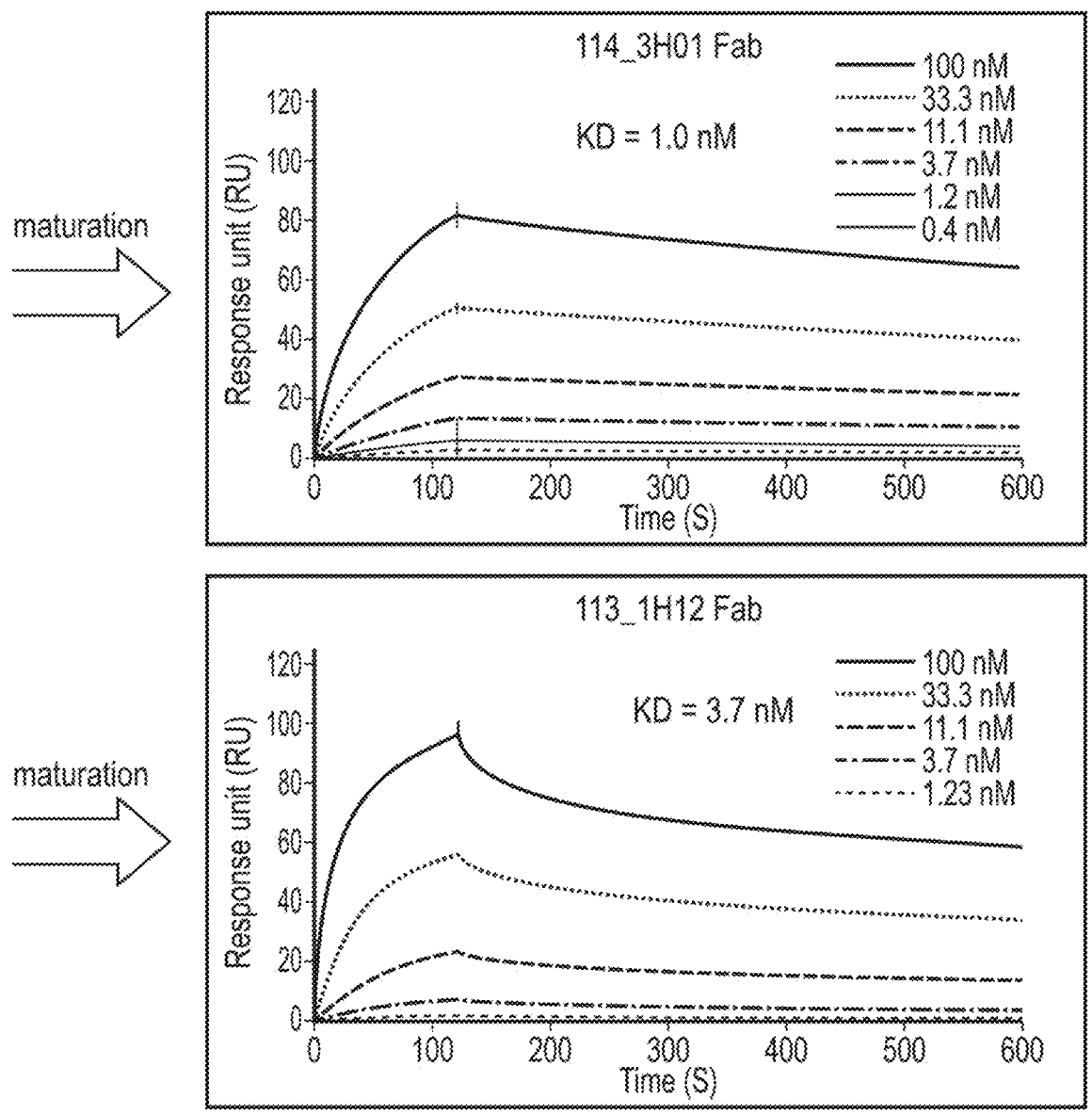

The lead anti-CXCL12 antibodies and their parent clones were subjected to a full kinetic analysis to determine the improvement in binding constants after affinity maturation. The binding of the Fab antibodies to biotinylated CXCL12 immobilised on a streptavidin chip was analysed using SPR (FIG. 3). Equilibrium dissociation constants (KD) of these antibodies were determined using a binding model appropriate for each binding interaction (FIGS. 3B and C). Of the four antibodies tested, 114_3H1 had the highest affinity to CXCL12 with a KD of 1 nM. This represents a 3800-fold improvement in affinity from its parent clone 093_2D06 (KD=3800 nM) after chain shuffling. Both 093_2A02 and its affinity matured variant 113_1H12 exhibited a biphasic binding profile with an initial fast dissociation phase followed by a much slower second dissociation phase. Such binding profiles are generally associated with binding interactions that involve antibody (or any other analyte) induced conformational change of the ligand resulting in a two-step binding. Two different preparations of both 113_1H13 and 092_2A02 were analysed by SPR. Similar results were obtained using both protein batches confirming that the observed binding profile was not an artefact or an issue with a particular protein preparation. The fact that only the antibodies from the same VH lineage exhibited biphasic binding favours the hypothesis that these antibodies might have a two-step binding mechanism. Hence the affinities of these antibodies were determined using a two-state binding model (FIG. 3C). The calculated binding affinities of 113_1H12 and 093_2D06 were 3.7 nM and 16.7 nM respectively, which represents a 4.5-fold improvement in affinity following light chain shuffling.

Inhibition of Cancer Cell Migration by Lead Anti-CXCL12 Antibodies

Figure 4:
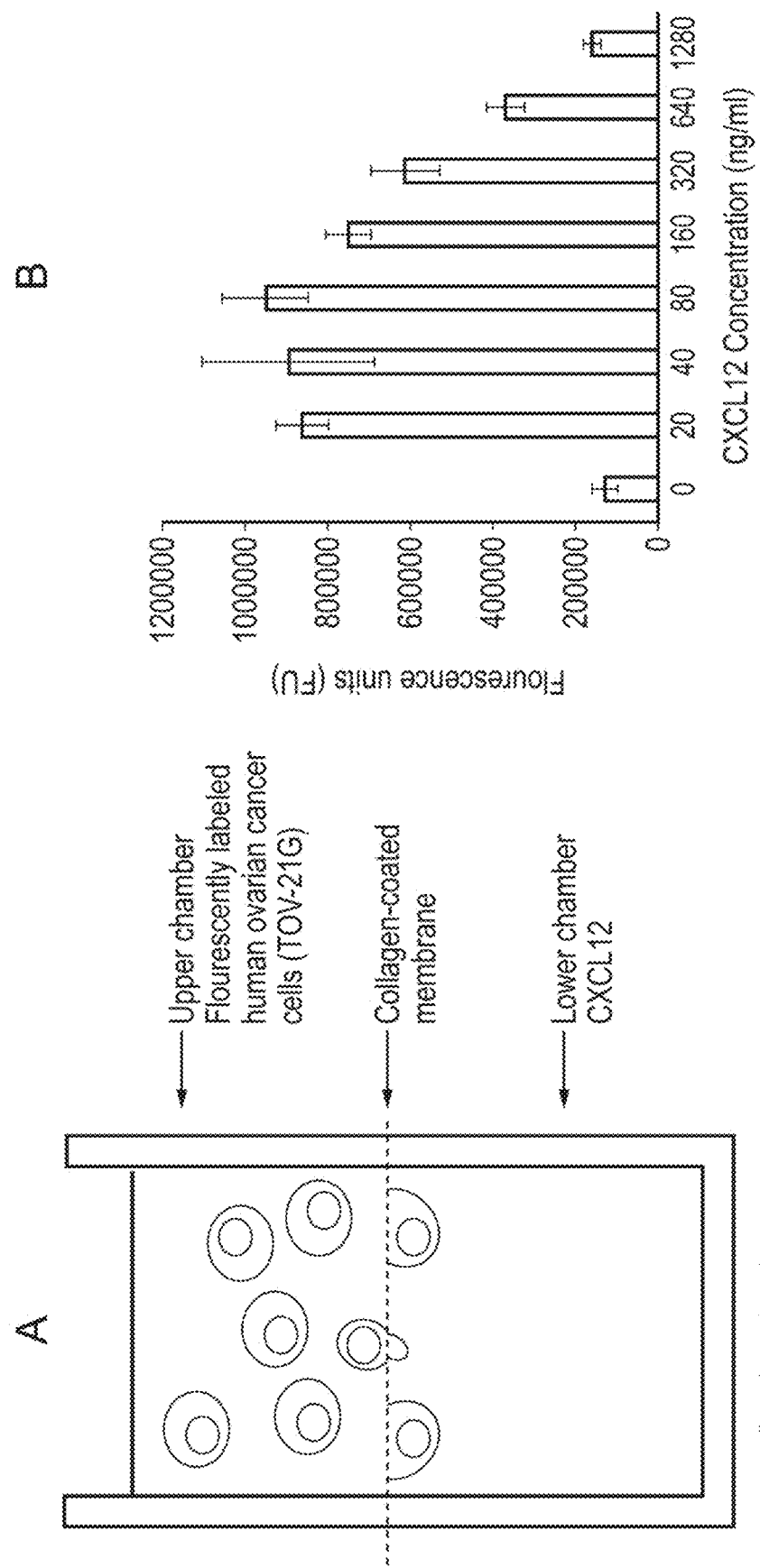
FIG. 4. CXCL12 induced migration of ovarian cancer cells. A) Fluorescently labelled human ovarian cancer cells (TOV-21G) in the upper chamber and CXCL12 in the lower chamber were separated by a porous membrane coated with collagen. Migration of cells across the membrane was quantified by fluorescence scanning. B) Optimum human CXCL12 concentration for inducing cell migration was determined by titration of CXCL12 (ranging from 20-1200 ng/ml). 80 ng/ml CXCL12 was chosen for stimulating cell migration in the inhibition assay. All error bars represent the standard deviation.

Migration of CXCR4 expressing cancer cells towards CXCL12 rich environments is one of the key factors promoting metastasis in many malignancies. The inhibition of CXCL12/CXCR4 dependent cancer cell migration is an important biological property of the therapeutic anti-CXCL12 antibody molecules of the present invention. Hence the lead antibodies 114_3H1 and 113_1H12 were tested for their ability to block CXCL12 induced migration of ovarian cancer cells using a transwell migration assay. The transwell migration assay used here was a modified version of the Boyden chamber assay used to study the chemotactic response of leukocytes. In this assay, migration of fluorescently labelled human ovarian cancer cells (TOV-21G) seeded in the upper chamber across a porous membrane and into the lower chamber containing CXCL12 was analysed (FIG. 4A). A previous study has shown that CXCL12 dimers are formed at higher concentrations, could inhibit cell migration. Therefore, the optimum CXCL12 concentration for stimulating cell migration was determined empirically (FIG. 4B).

Figure 5:
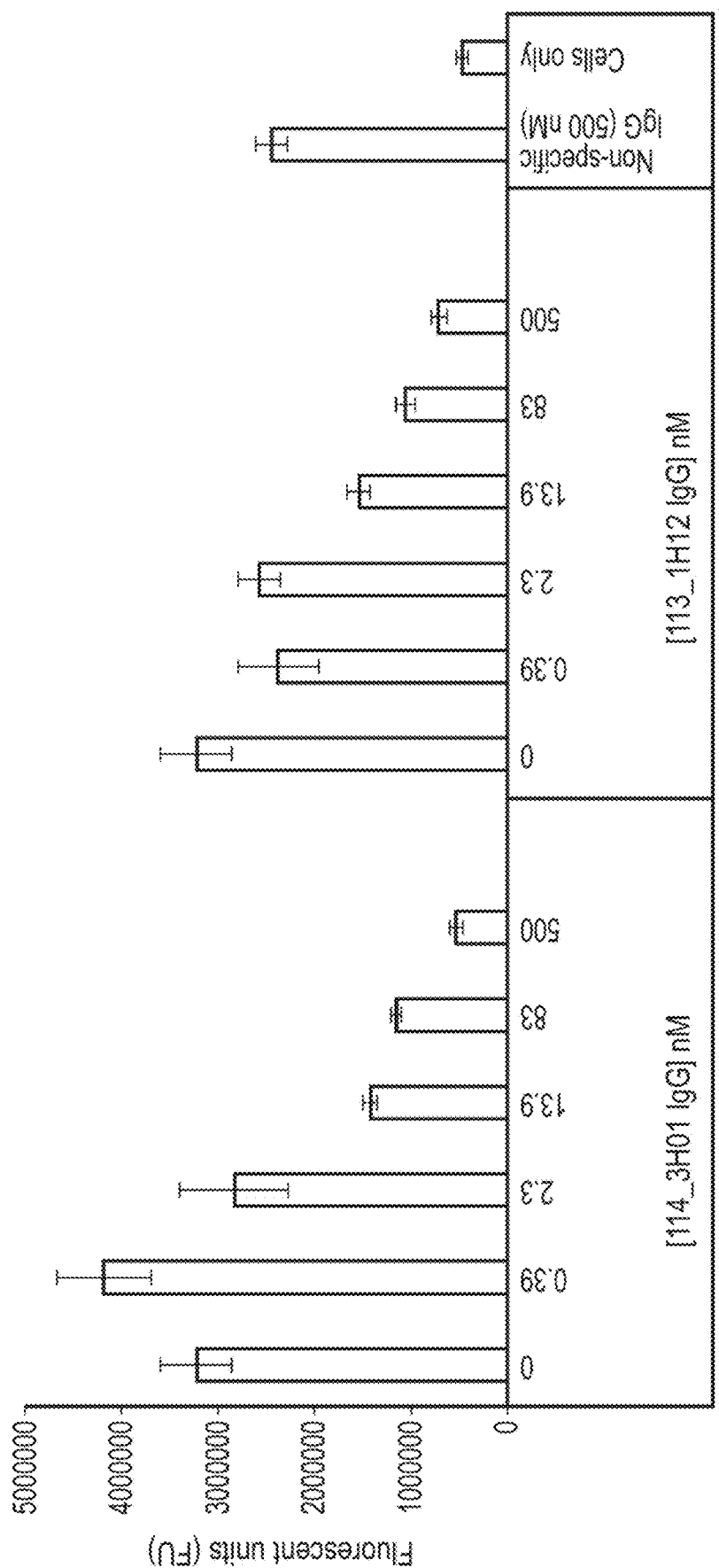
FIG. 5. Inhibition of cancer cell migration by anti-CXCL12 antibodies. Transwell migration of fluorescently labelled TOV-21G cells towards CXCL12 was quantified using fluorescence scanning. Titrations of 114_3H1 (labelled as 114_3H01) and 113_1H12 IgGs ranging from 0.39-500 nM were mixed with 80 ng/ml (10 nM) human CXCL12 in the lower chamber to test the impact of these antibodies on CXCL12 induced migration. An anti-lysozyme antibody (500 nM) was used as an isotype control. All error bars represent standard deviation.

In order to assess the ability of the lead anti-CXCL12 antibodies to inhibit CXCL12 induced migration of ovarian cancer cells, titration of 114_3H1 IgG and 113_1H12 IgG were carried out in the transwell migration assay described above. Both antibodies inhibit the migration of TOV-21G cells in a dose dependent manner (FIG. 5). The half maximal inhibitory concentration ($IC_H$) of 114H01 and 113_1H12 were 4.6 (±0.5) nM and 13.2 (±4.1) nM respectively. These values are in accordance with the equilibrium dissociation constants determined by SPR. Further replicate experiments produced higher quality data that confirmed that the 1050 values for 114H01 and 113_1H12 were 5 nM and 9 nM respectively.

Inhibition of Angiogenesis by Lead Anti-CXCL12 Antibodies

The survival and proliferation of tumours is greatly dependent on a supportive vascular network that provides adequate supply of oxygen and nutrients. The CXCL12/CXCR4 axis plays a key role in promoting the formation of new blood vessels (angiogenesis) to establish a tumour supportive vasculature. CXCL12 and CXCR4 form a positive feed back loop with VEGF, a well-known pro-angiogenic factor. In this loop, VEGF stimulates the expression of both CXCL12 and CXCR4. Conversely, CXCL12 induced activation of CXCR4 up-regulates production of VEGF by endothelial cells. Hence the lead anti-CXCL12 antibodies were tested in an in vitro angiogenesis assay to evaluate their ability to inhibit the formation and branching of tubules.

Figure 6A:
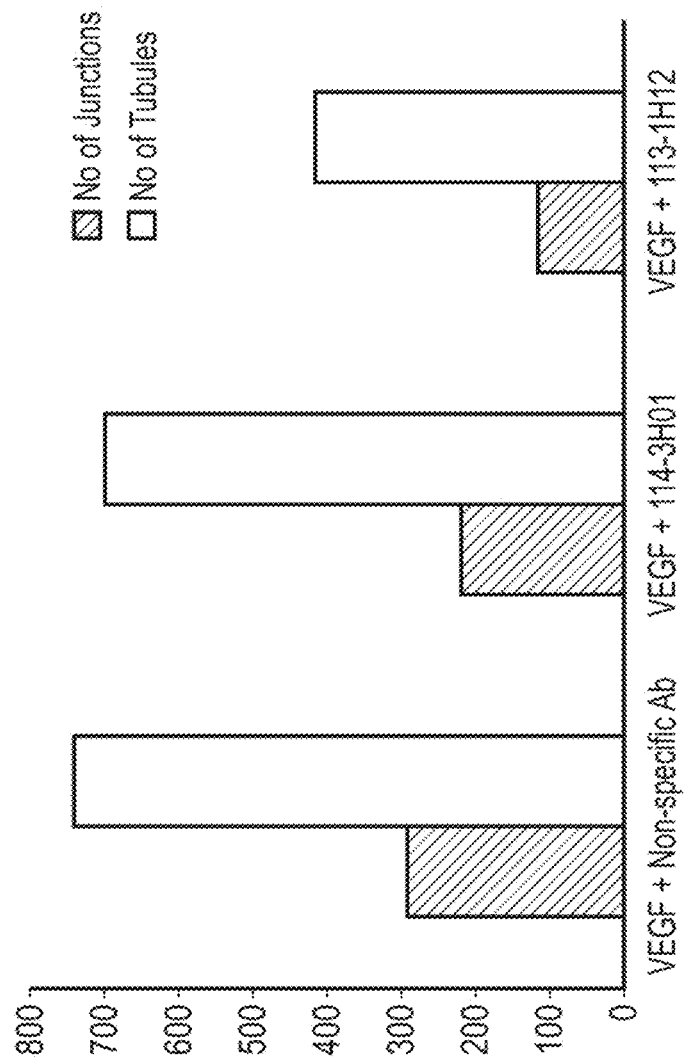
FIG. 6. Inhibition of angiogenesis by anti-CXCL12 antibodies. Human umbilical vein endothelial cells (HUVECs) were plated onto fibroblasts that had been grown for 6 days on gelatin coated chamber slides. These two cell types were co-cultured for 7 days in a media containing VEGF and lead anti-CXCL12 antibodies 114_3H1 and 113_1H12. An IgG that bind to lysozyme (Non-specific IgG) was used as an isotype control for the assay (panel A). After 7 days of co-culture the cells were stained for the platelet/endothelial adhesion molecule-1 (PECAM-1, a marker for angiogenesis) to visualise the formation and branching of tubules by light microscopy. Total number of tubules, number of branch junctions (FIG. 6A) and the total tubule length (FIG. 6B) was calculated using AngioSys image analysis software.

In this assay, human umbilical vein endothelial cells (HUVECs) and fibroblasts were cultured together in a media containing anti-CXCL12 antibodies and VEGF. The interaction of these two cell types in the presence of VEGF results in the formation of three-dimensional tubes that resemble small capillaries in vivo. Inhibitory effects of anti-CXCL12 antibodies were analysed after 7 days of co-culture by immunohistochemistry (FIG. 6).

Figure 6B:
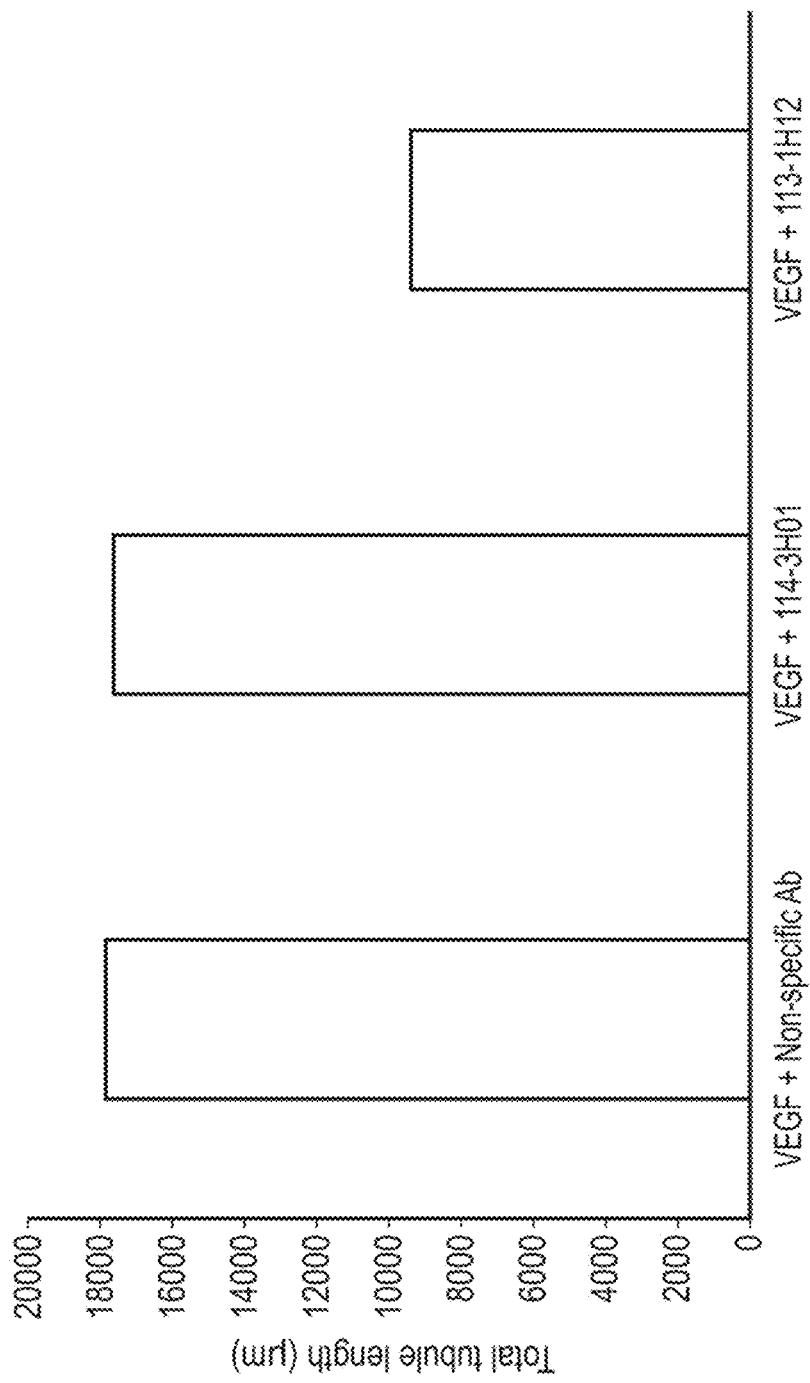
Figure 9A:
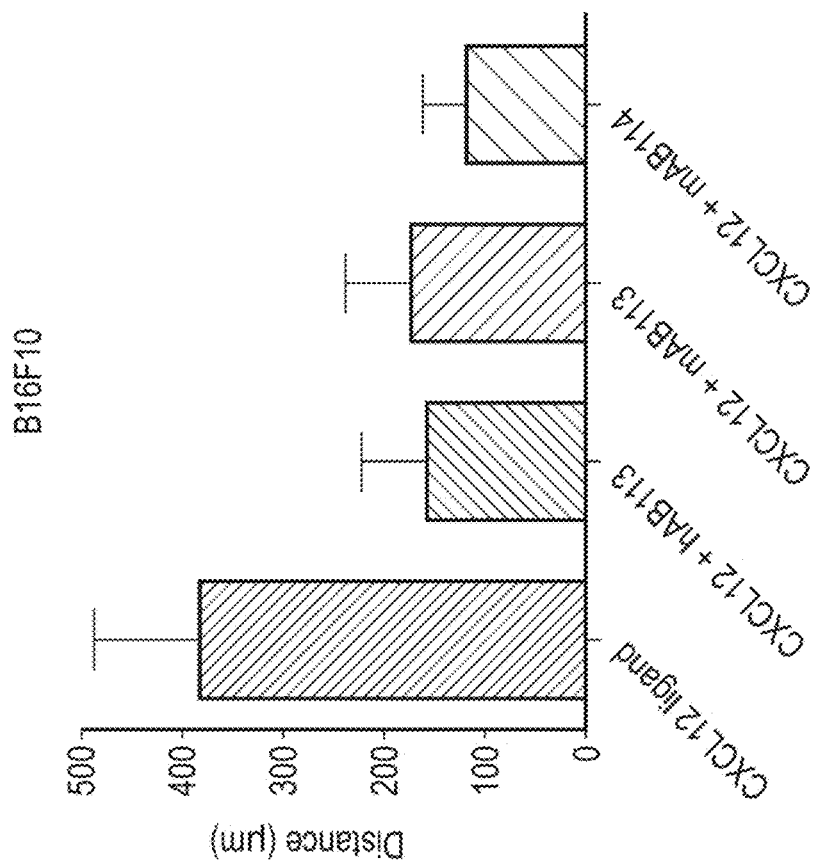
FIGS. 9A & B. Migration tracks showing the results of experiments to determine the effectiveness of the antibodies (113_1H12 in a human IgG2 format (hAB113), 113_1H12 in a chimeric murine IgG2a format (mAB113) and 114_3H1 in a chimeric murine IgG2a format (mAB114)) in blocking migration of a murine metastatic melanoma cell line (B16F10) and human ovarian carcinoma cell line (TOV-21) in the presence of human CXCL12.
Figure 9B:
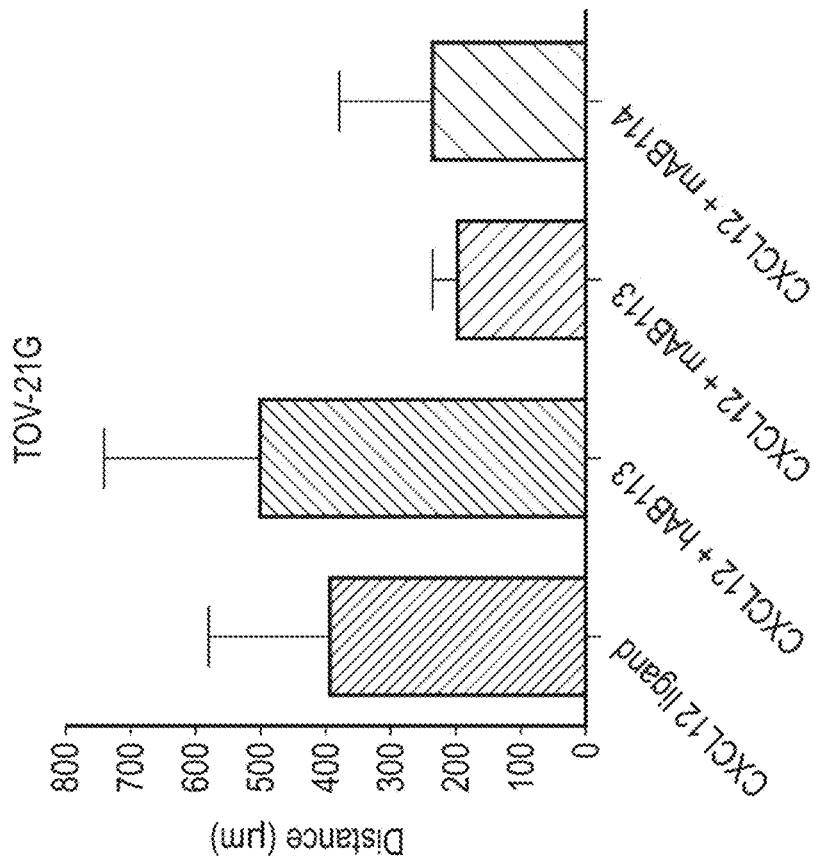
Figure 10A:
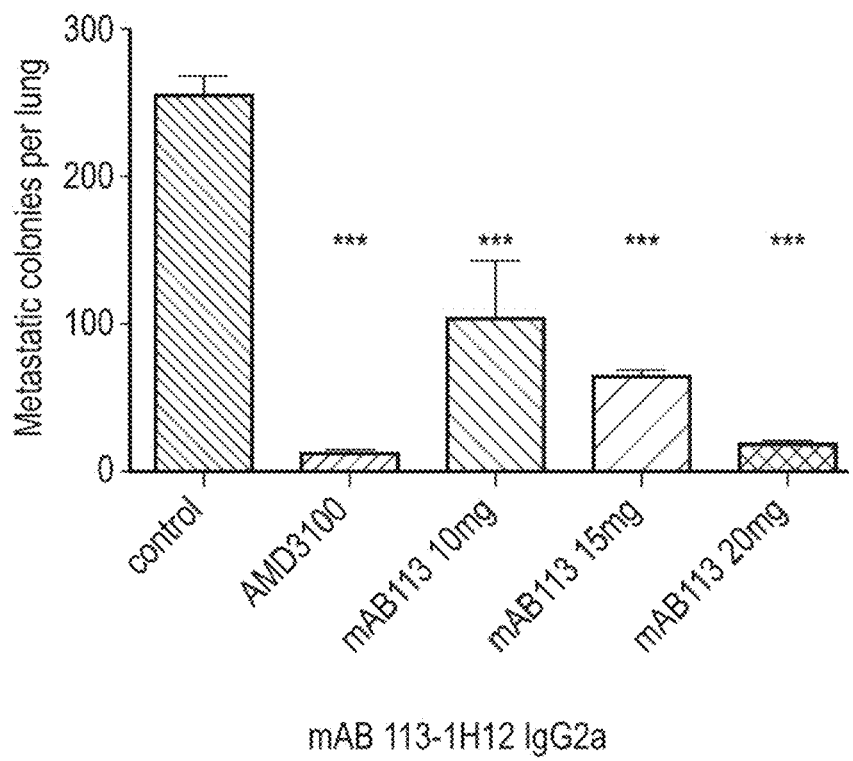
FIGS. 10A-10B. Results of in vivo experimental metastasis model cell migration assay based B16F10 melanoma cells requiring CXCR4 for migration to the lung and initiation of metastasis. B16F10 melanoma cells were introduced into C57B1 mice through tail vein injection on day 0 and treatment commenced on day 1. Treatment regimes were either 5 mg/kg of the clinical CXCR4 inhibitor AMD3100 (Plerixafor) twice daily or twice a week with either 10, 15 or 20 mg/kg of the anti-CXCL12 antibody mAB 113-1H12 (FIG. 10A) or mAB 114-3H1 (FIG. 10B) in a chimeric murine IgG2a format. Mice in the control arm were treated twice a week with 20 mg/kg of a control antibody. All mice were culled on day 14 and the number of metastatic colonies in the lungs quantified. A level of inhibition equivalent to that of AMD3100 was achieved with the 20 mg/kg dose of 113_1H12.
Figure 10B:
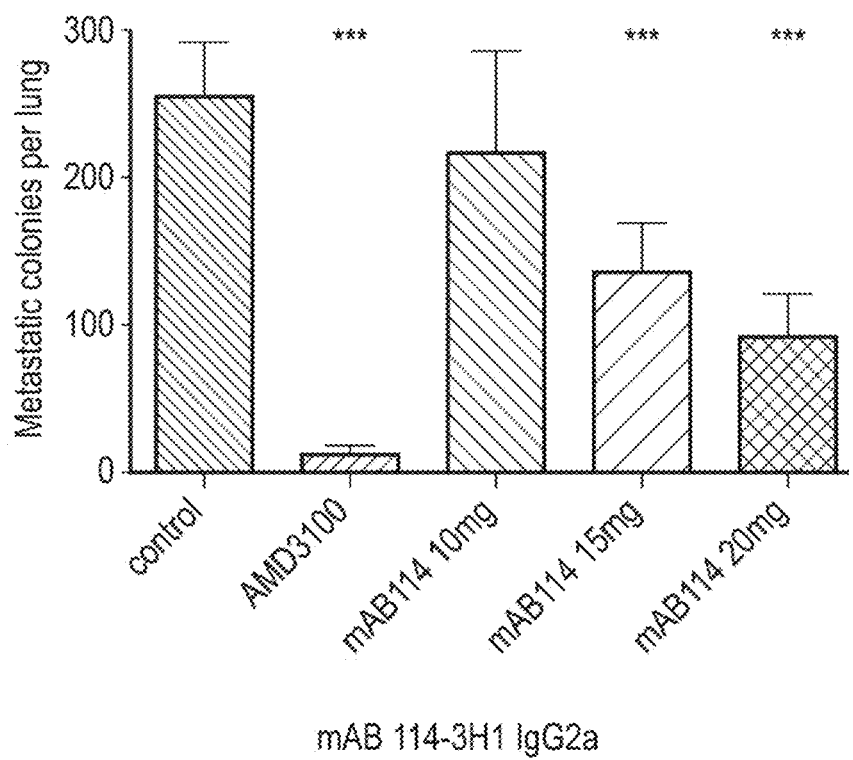

The most valuable parameters for analysing angiogenesis are the tubule length and the number branches per tubule. Endothelial cells form long and branched tubules upon VEGF stimulation and this was unaffected by the presence of a non-specific antibody. significant inhibition of tubule formation and branching was observed with 113_1H12 (FIG. 6B).

Comparison with Antibodies of WO 2008/018641

WO 2008/018641 describes two pairs of anti-CXCL12 antibodies, 1D3 and 1H2 and 106 and 2A5. The pairs of antibodies recognise common epitopes in CXCL12.

Figure 8:
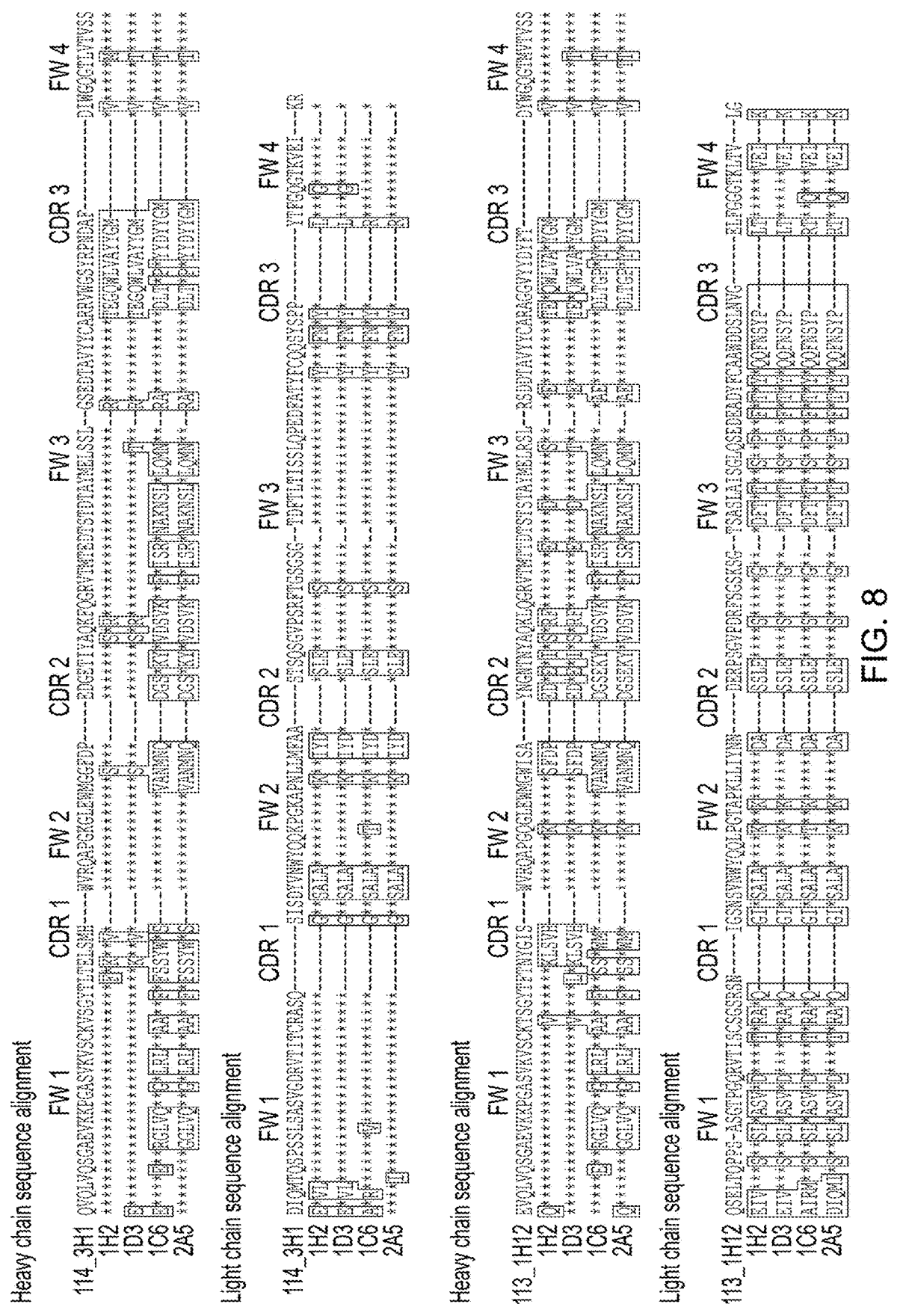

The sequences of the heavy and light chains of the antibodies of WO 2008/018641 were aligned with the sequences of the antibodies of the present invention and the alignment is shown in FIG. 8. This shows that there are significant differences in the CDR sequences of these antibodies as compared to antibodies 114_H01 and 113_1H12 of the present invention.

The affinity of the antibodies was also compared. The affinity constant ($K_D$) for human CXCL12 of antibody 114_H01 was 2.4 nM and that of antibody 113_1H12 was 4.2 nM. This compares to the values reported for the antibodies of WO 2008/018641 of 1D3 $K_D$=151 nM; 1H2 $K_D$=176 nM; 106 $K_D$=3.6 nM and 2A5 $K_D$=4.6 nM. The affinity data shows that the antibodies 114H01 and 113_1H12 of the present invention have affinities that are as good or better than the best results reported for the antibodies of WO 2008/018641 despite using Fab format antibodies rather than IgG which would in general lead to an underestimate of the affinity of the antibodies of the present invention relative to the prior art.

Epitope Mapping

The epitopes bound by antibodies 113_1H12 and 114_H01 were compared to the epitope bound by the four exemplified antibodies disclosed in WO 2008/018641. These experiments showed that 113_1H12 partially shares an epitope with the antibodies 1D3 and 1H2 of WO 2008/018641, while 114_3H1 has a unique epitope that shares only one residue with the antibodies of WO 2008/018641.

E15 is outside of regions that involved in receptor or heparin binding. All other epitope residues are within regions involved in receptor binding, which according to numbering of the full length protein at UniProt P48061 (SDF1 HUMAN) are 29-33, 39-41, 48-50, 60-70). WO 2008/018641 discloses that the residues involved in receptor binding lie between amino acid residues 7-19.

| Antibody | Substitutions that strongly reduce/eliminate binding | Substitutions that partially reduce binding |
|---|---|---|
| 114_3H1 | P10A, R12A | E15A, I28A, P32A, N45A, K54A |
| 113_1H12 | P10A, Q48A | K54A, N45A |
| 1D3 and 1H2 | P10A, N45A, Q48A | |
| 2A5 and 1C6 | P10A, E15A, N45A, R47A | F13A, I28A, K54A |

Properties of Anti-CXCL12 Monoclonal Antibodies in a Chimeric Murine IgG2a Backbone The variable regions of the 113_1H12 and 114_3E1 were cloned into an murine IgG2a expression system, permitting production of the chimeric antibodies, with murine constant regions and human variable regions. This type of chimeric antibody could be preferable for in vivo testing in immunocompetent animals to reduce immune response towards the antibody which could occur upon administration of a fully human antibody.

A) Migration Assays.

The ability of the antibodies in a chimeric murine IgG2a and a fully human IgG2 formats to block cellular migration of human and murine cell lines was investigated using a murine metastatic melanoma cell line (B16F10) and a human ovarian carcinoma cell line (TOV21G).

All antibodies were used at a concentration of 50 μg/ml. The human CXCL12 ligand (Peprotech) was used at a concentration of 500 ng/ml. Antibodies and ligands were prepared in DMEM (for B16F10 studies) or RPMI (for TOV21G studies). For each time-lapse migration assay $3\text{-}4\times10^6$ cells were used in a collagen-cell mix inside a coverslip migration chamber. Cell suspensions were combined with a collagen mix in a ratio of 1 (cells):2 (collagen). The collagen mix was composed of sodium bicarbonate. 10×MEM and Collagen (3 mg/ml, Sigma) in a 1:2:15 ratio. The antibodies were added to the cell-collagen mix and the resulting mixture was inserted into the migration chamber where the collagen was polymerised by incubation at 37° C. for 30 minutes. Once polymerised the CXCL12 ligand was added to produce the chemokine gradient and movement of the cells towards CXCL12 was determined using time-lapse imaging. Images were taken at an interval of 1 picture/min over a period of 3.5-4 hours. Time lapse imagining permit the visualisation of cellular migration tracks which were them analysed using Image J software to determine the extent of cellular migration.

The migration distance for B16F10 cells in the presence of CXCL12 and the 3 blocking antibodies are shown in FIGS. 9A and B.

All antibodies, 113_1H12 in a human IgG2 format (hAB113), 113_1H12 in a chimeric murine IgG2a format (mAB113) and 114_3H1 in a chimeric murine IgG2a format (mAB114), were effective at substantially blocking cellular migration in B16F10 cells and to some degree also in TOV-21 cells. In this assay 113_1H12 in a human IgG2 format (hAB113) was inactive in terms of blocking TOV21G cell migration whereas mAB113 was fully active and mAB114 somewhat in between. However, from the results in FIG. 5 we know that the 113_1H12 antibody in a human IgG2 format can inhibit the migration of the TOV21G cell line towards CXCL12 and so the inactive result here is likely to be an anomaly. These results are summarised in FIG. 9A.

In addition, all three antibodies were effective at inhibiting CXCL12 dependent migration of B16F10 cells. This is shown graphically in FIG. 9B. Thus, these experiments confirm that the antibodies in a chimeric murine IgG2a format work in in vitro migration assays and are capable of inhibiting cancer cell migration.

B) Serum Stability Testing.

The serum stability of the antibodies 114_3H1 and 113_1H12 in a chimeric murine IgG2a format was tested. Serum stability assays were performed using human serum. Antibodies were incubated in serum at a concentration of 100 μg/ml for 6, 12, 24 and 48 hours. Serum containing antibodies were diluted to a concentration of 50 μg/ml in DMEM or RPMI and used for the time-lapse migration assay as described above in A. These experiments found that the antibodies in a chimeric murine IgG2a format were stable over 48 hours in serum and were still active at inhibiting CXCL12-dependent B16F10 cell migration after 48 hours in serum. This confirms that both antibodies are very stable in serum.

C) In Vivo Pulmonary Metastasis.

B16F10 melanoma cells require CXCR4 for migration to the lung and initiation of metastasis. A simple experimental metastasis in vivo model was used to evaluate the ability of the chimeric murine IgG2a antibodies to interfere with CXCL12 and therefore block metastatic development. B16F10 melanoma cells were introduced into C57B1 mice through tail vein injection on day 0 and treatment commenced on day 1. Treatment regimes were either 5 mg/kg of the clinical CXCR4 inhibitor AMD3100 (Plerixafor) twice daily or twice a week with either 10, 15 or 20 mg/kg of the anti-CXCL12 antibody in a murine IgG2a format. Mice in the control arm were treated twice a week with 20 mg/kg of a murine IgG2a control antibody. All mice were culled on day 14 and the number of metastatic colonies in the lungs quantified by manual counting. As shown in FIG. 10, both chimeric murine 114_3H1 and 113_1H12 antibodies were active at inhibiting metastatic development. In particular, antibody 113_1H12 was more potent and resulted in and inhibition at 20 mg/kg equivalent to that seen with 5 mg/kg of the small molecule antagonist of CXCR4, AMD3100. Thus, both antibodies are active in vivo in inhibiting CXCR4 dependent-pulmonary metastasis.

SEQUENCE LISTING

```
Antibody 114_3H1
SEQ ID NO: 1: CDR-H1 amino acid sequence (from Ab114_3H1)
ELSMH SEQ ID NO: 2: CDR-H2 amino acid sequence (from Ab114_3H1)
```

GFDPEDGETIYAQKFQG

SEQ ID NO: 3: CDR-H3 amino acid sequence (from Ab114_3H1)
RVWGSYRPNDAFDI

SEQ ID NO: 4: CDR-L1 amino acid sequence (from Ab114_3H1)
RASQSISDYVN

SEQ ID NO: 5: CDR-L2 amino acid sequence (from Ab114_3H1)
AASTSQS

SEQ ID NO: 6: CDR-L3 amino acid sequence (from Ab114_3H1)
QQSYSPPYT

SEQ ID NO: 7: VH domain amino acid sequence
114_3H1 Variable Heavy chain
QVQLVQSGAEVKKPGASVKVSCKVSGYTLT<u>ELSMH</u>WVRQAPGKGLEWMG<u>GFDPEDGETIYAQKFQ GR</u>VTMTEDTSTDTAYMELSSLGSEDTAVYYCAR<u>RVWGSYRPNDAFDI</u>WGQGTLVTVSS SEQ ID NO: 8: VH domain nucleic acid sequence
>114_3H1_VH
CAGGTCCAGCTGGTACAGTCTGGGGCTGAGGTGAAGAAGCCTGGGGCCTCAGTGAAGGTCTCCTG

CAAGGTTTCCGGATACACCCTCACTGAATTATCCATGCACTGGGTGCGACAGGCTCCTGGAAAAG

GGCTTGAGTGGATGGGAGGTTTTGATCCTGAAGATGGTGAAACAATCTACGCACAGAAGTTCCAG

GGCAGAGTCACCATGACCGAGGACACATCTACAGACACAGCCTACATGGAGCTGAGCAGCCTGGG

ATCTGAGGACACGGCCGTGTATTACTGTGCGAGACGCGTTTGGGGAGTTATCGCCCCAATGATG

CTTTTGATATCTGGGGCCAAGGAACCCTGGTCACCGTCTCCTCA

SEQ ID NO: 9: VL domain amino acid sequence
114_3H1 Variable Light chain
DIQMTQSPSSLSASVGDRVTITC<u>RASQSISDYVN</u>WYQQKPGKAPNLLMF<u>AASTSQS</u>GVPSRFTGS GSGTDFTLTISSLQPEDFATYFC<u>QQSYSPPYT</u>FGQGTKVEIKR SEQ ID NO: 10: VL domain nucleic acid sequence
>114_3H1_VL
GACATCCAGATGACCCAGTCTCCATCCTCCCTGTCTGCATCTGTAGGCGACAGAGTCACCATCAC

TTGCCGGGCAAGTCAGAGCATAAGCGACTATGTAAACTGGTATCAGCAGAAACCAGGGAAAGCCC

CCAACCTCCTGATGTTTGCTGCATCCACTTCGCAAAGTGGGGTCCCGTCAAGGTTCACTGGCAGC

GGATCTGGGACAGATTTCACTCTCACCATCAGGAGTCTGCAACCTGAAGATTTTGCAACTTACTT

CTGTCAACAGAGTTACAGTCCGCCCTACACTTTTGGCCAGGGGACCAAGGTGGAGATCAAACGT

SEQ ID NO: 11: 114_3H1 scFv
Lead antibody sequence
>114_3H1
QVQLVQSGAEVKKPGASVKVSCKVSGYTLT<u>ELSMH</u>WVRQAPGKGLEWMG<u>GFDPEDGETIYAQKFQ GR</u>VTMTEDTSTDTAYMELSSLGSEDTAVYYCAR<u>RVWGSYRPNDAFDI</u>WGQGTLVTVSSLEGGGGS GGGGSGGGGASDIQMTQSPSSLSASVGDRVTITC<u>RASQSISDYVN</u>WYQQKPGKAPNLLMF<u>AASTSQ S</u>GVPSRFTGSGSGTDFTLTISSLQPEDFATYFC<u>QQSYSPPYT</u>FGQGTKVEIKRAAASAHHHHHHK

LDYKDHDGDYKDHDIDYKDDDDK

Antibody 113_1H12
SEQ ID NO: 12: CDR-H1 amino acid sequence 113_1H12
NYGIS

SEQ ID NO: 13: CDR-H2 amino acid sequence 113_1H12
WISAYNGNTNYAQKLQG

SEQ ID NO: 14: CDR-1-13 amino acid sequence 113_1H12
AGGVYYDYFTDY

SEQ ID NO: 15: CDR-L1 amino acid sequence 113_1H12
SGSRSNIGSNSVN

SEQ ID NO: 16: CDR-L2 amino acid sequence 113_1E12
NNDERPS

-continued

SEQ ID NO: 17: CDR-L3 amino acid sequence 113_1H12
AAWDDSLNVGEL

SEQ ID NO: 18: VH domain amino acid sequence
113_1H12 Variable Heavy chain
EVQLVQSGAEVKKPGASVKVSCKTSGYTFT<u>NYGIS</u>WVRQAPGQGLEWMG<u>WISAYNGNTNYAQKLQ</u>

<u>G</u>RVTMTTDTSTSTAYMELRSLRSDDTAVYYCAR<u>AGGVYYDYFTDY</u>WGQGTMVTVSS

SEQ ID NO: 19: VH domain nucleic acid sequence
>113_1H12_VH
ATGGCCGAGGTGCAGCTGGTGCAGTCTGGAGCTGAGGTGAAGAAGCCTGGGGCCTCAGTGAAGGT

CTCCTGCAAGACTTCTGGTTACACCTTTACCAACTATGGTATCAGCTGGGTGCGACAGGCCCCTG

GACAAGGGCTTGAGTGGATGGGATGGATCAGCGCTTACAATGGTAACACGAACTATGCACAGAAG

CTCCAGGGCAGAGTCACCATGACCACAGACACATCCACGAGCACAGCCTACATGGAGCTGAGGAG

CCTGAGATCTGACGACACGGCCGTGTATTACTGCGCGAGAGCCGGCGGAGTCTATTACGATTATT

TCACGGACTACTGGGGCCAGGGGACAATGGTCACCGTCTCTTCA

SEQ ID NO: 20: VL domain amino acid sequence
113_1H12 Variable Light chain
QSELTQPPSASGTPGQRVTISC<u>SGSRSNIGSNSVN</u>WYQQLPGTAPKLLIY<u>NNDERPS</u>GVPDRFSG SKSGTSASLAISGLQSEDEADYFC<u>AAWDDSLNVGEL</u>FGGGTKLTVLG SEQ ID NO: 21: VL domain nucleic acid sequence
>113_1H12_VL
CAGTCTGAGCTGACTCAGCCACCCTCAGCGTCTGGGACCCCCGGGCAGAGGGTCACCATCTCTTG

TTCTGGAAGCCGCTCCAACATCGGAAGTAATTCTGTAAACTGGTACCAGCAGCTCCCAGGAACGG

CCCCCAAACTCCTCATTTATAATAATGATGAGCGGCCCTCAGGGGTCCCTGACCGATTCTCTGGC

TCCAAGTCTGGCACCTCAGCCTCCCTGGCCATCAGTGGGCTCCAGTCTGAGGATGAGGCTGATTA

TTTCTGTGCAGCATGGGATGACAGCCTGAATGTCGGGGAGCTATTCGGCGGAGGGACCAAGCTGA

CCGTCCTAGGT

SEQ ID NO: 22: 113_1H12 scEv
Lead antibody sequence
>113_1H12_scFv
EVQLVQSGAEVKKPGASVKVSCKTSGYTFT<u>NYGIS</u>WVRQAPGQGLEWMG<u>WISAYNGNTNYAQKLQ</u>

<u>G</u>RVTMTTDTSTSTAYMELRSLRSDDTAVYYCAR<u>AGGVYYDYFTDY</u>WGQGTMVTVSSLEGGGGSGG

GGSGGGASQSELTQPPSASGTPGQRVTISC<u>SGSRSNIGSNSVN</u>WYQQLPGTAPKLLIY<u>NNDERPS</u>

GVPDRFSGSKSGTSASLAISGLQSEDEADYF<u>CAAWDDSLNVGEL</u>FGGGTKLTVLGAAASAHHHHH

HKLDYKDHDGDYKDHDIDYKDDDDK

SEQ ID NO: 23 : CXCL12 amino acid sequence (full length sequence)
>sp|P48061-2|SDF1_HUMAN Isoform Alpha of Stromal cell-derived
factor 1 OS = Homo sapiens GN = CXCL12
MNAKVVVVLVLVLTALCLSDGKPVSLSYRCPCRFFESHVARANVKHLKILNTPNCALQIVARLKN

NNRQVCIDPKLKWIQEYLEKALNK

SEQ ID NO: 24 : Synthesised CXCL12 amino acid sequence used for
antibody selection. Corresponds to amino acids 22 to 89 of full
length CXCL12 protein
KPVSLSYRCPCRFFESHVARANVKHLKILNTPNCALQIVARLKNNNRQVCIDPKLKWIQEYLEKA

LNK

SEQ ID NO: 25: recombinant "wild-type" CXCL12 expressed in
E. coli for epitope mapping (including His tag and linker)
KPVSLSYRCPCRFFESHVARANVKHLKILNTPNCALQIVARLKNNNRQVCIDPKLKWIQEYLEKA

LNKAAASAHHHHHHKL

REFERENCES

All documents mentioned in this specification are incorporated herein by reference in their entirety.

The invention claimed is:

1. An isolated anti-CXCL12 antibody molecule which specifically binds to human CXCL12, wherein the antibody molecule comprises
    (a) a heavy chain complementarity-determining region 1 (CDR-H1) having the amino acid sequence of NYGIS (SEQ ID NO: 12),
    (b) a heavy chain complementarity-determining region 2 (CDR-H2) having the amino acid sequence of WISAYNGNTNYAQKLQG (SEQ ID NO: 13),
    (c) a heavy chain complementarity-determining region 3 (CDR-H3) having the amino acid sequence of AGGVYYDYFTDY (SEQ ID NO: 14),
    (d) a light chain complementarity-determining region 1 (CDR-L1) having the amino acid sequence of SGSRSNIGSNSVN (SEQ ID NO: 15),
    (e) a light chain complementarity-determining region 2 (CDR-L2) having the amino acid sequence of NNDERPS (SEQ ID NO: 16), and
    (f) a light chain complementarity-determining region 3 (CDR-L3) having the amino acid sequence of AAWDDSLNVGEL (SEQ ID NO: 17).

2. The anti-CXCL12 antibody molecule of claim 1, wherein the antibody molecule is a complete antibody, a monoclonal antibody, a Fab fragment, a F(ab')$_2$ fragment, a scFv, a scFv-Fc, an intrabody, a diabody, a triabody, a bispecific antibody or a chimeric antibody.

3. The anti-CXCL12 antibody molecule of claim 1, wherein the antibody molecule is a human antibody.

4. An immunoconjugate comprising an antibody molecule according to claim 1.

5. The immunoconjugate of claim 4, wherein the antibody molecule is conjugated to therapeutically active moiety.

6. The immunoconjugate of claim 5, wherein the therapeutically active moiety is a cytotoxic moiety or an immunostimmulatory moiety.

7. The immunoconjugate of claim 4, wherein the antibody molecule is conjugated to a cytotoxic moiety and the cytotoxic moiety is an alkylating agent, an alkaloid, a platinum coordination complex, a cytotoxic peptide, a radioactive agent, or a pro-drug capable of conversion into a cytotoxic moiety.

8. A pharmaceutical composition comprising an antibody molecule according to claim 1, or an immunoconjugate thereof, and a pharmaceutically acceptable excipient.

9. A method of treating an individual with a CXCL12-mediated cancer comprising administering an antibody molecule according to claim 1, or an immunoconiugate thereof, to an individual in need thereof.

10. An anti-CXCL12 antibody molecule comprising:
    a variable heavy chain (VH) polypeptide having the amino acid sequence of SEQ ID NO: 18, and
    a variable light chain (VL) polypeptide having the amino acid sequence of SEQ ID NO: 20, wherein the antibody molecule specifically binds to human CXCL12 and inhibits CXCL12-mediated biological activity.

11. The anti-CXCL12 antibody molecule of claim 10, wherein the antibody molecule is a complete antibody, a monoclonal antibody, a Fab fragment, a F(ab')2 fragment, a scFv, a scFv-Fc, an intrabody, a diabody, a triabody, a bispecific antibody or a chimeric antibody.

12. An immunoconjugate comprising an antibody molecule according to claim 10.

13. The immunoconjugate of claim 12, wherein the antibody molecule is conjugated to therapeutically active moiety.

14. The immunoconjugate of claim 13, wherein the therapeutically active moiety is a cytotoxic moiety or an immunostimmulatory moiety.

15. The immunoconjugate of claim 12, wherein the antibody molecule is conjugated to a cytotoxic moiety and the cytotoxic moiety is an alkylating agent, an alkaloid, a platinum coordination complex, a cytotoxic peptide, a radioactive agent, or a pro-drug capable of conversion into a cytotoxic moiety.

16. A pharmaceutical composition comprising an antibody molecule according to claim 10, or an immunoconiugate thereof, and a pharmaceutically acceptable excipient.

17. A method of treating an individual with a CXCL12-mediated cancer comprising administering an antibody molecule according to claim 10, or an immunoconiugate thereof, to an individual in need thereof.

* * * * *

SEQUENCE LISTING

<160> NUMBER OF SEQ ID NOS: 53

<210> SEQ ID NO 1
<211> LENGTH: 5
<212> TYPE: PRT
<213> ORGANISM: Artificial sequence
<220> FEATURE:
<223> OTHER INFORMATION: CDR-H1 amino acid sequence (from Ab114_3H1)

<400> SEQUENCE: 1

Glu Leu Ser Met His
1               5

<210> SEQ ID NO 2
<211> LENGTH: 17
<212> TYPE: PRT
<213> ORGANISM: Artificial sequence
<220> FEATURE:
<223> OTHER INFORMATION: CDR-H2 amino acid sequence (from Ab114_3H1)

<400> SEQUENCE: 2

Gly Phe Asp Pro Glu Asp Gly Glu Thr Ile Tyr Ala Gln Lys Phe Gln
1               5                   10                  15

Gly

<210> SEQ ID NO 3
<211> LENGTH: 14
<212> TYPE: PRT
<213> ORGANISM: Artificial sequence
<220> FEATURE:
<223> OTHER INFORMATION: CDR-H3 amino acid sequence (from Ab114_3H1)

<400> SEQUENCE: 3

Arg Val Trp Gly Ser Tyr Arg Pro Asn Asp Ala Phe Asp Ile
1               5                   10

<210> SEQ ID NO 4
<211> LENGTH: 11
<212> TYPE: PRT
<213> ORGANISM: Artificial sequence
<220> FEATURE:
<223> OTHER INFORMATION: CDR-L1 amino acid sequence (from Ab114_3H1)

<400> SEQUENCE: 4

Arg Ala Ser Gln Ser Ile Ser Asp Tyr Val Asn
1               5                   10

<210> SEQ ID NO 5
<211> LENGTH: 7
<212> TYPE: PRT
<213> ORGANISM: Artificial sequence
<220> FEATURE:
<223> OTHER INFORMATION: CDR-L2 amino acid sequence (from Ab114_3H1)

<400> SEQUENCE: 5

Ala Ala Ser Thr Ser Gln Ser
1               5

<210> SEQ ID NO 6
<211> LENGTH: 9
<212> TYPE: PRT
<213> ORGANISM: Artificial sequence
<220> FEATURE:
<223> OTHER INFORMATION: CDR-L3 amino acid sequence (from Ab114_3H1)

<400> SEQUENCE: 6

Gln Gln Ser Tyr Ser Pro Pro Tyr Thr
1               5

<210> SEQ ID NO 7
<211> LENGTH: 123
<212> TYPE: PRT
<213> ORGANISM: Artificial sequence
<220> FEATURE:
<223> OTHER INFORMATION: VH domain amino acid sequence

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Gly Ser Glu Asp Thr Ala Val Tyr Tyr Cys
                85                  90                  95

Ala Arg Arg Val Trp Gly Ser Tyr Arg Pro Asn Asp Ala Phe Asp Ile
            100                 105                 110

Trp Gly Gln Gly Thr Leu Val Thr Val Ser Ser
        115                 120

<210> SEQ ID NO 8
<211> LENGTH: 369
<212> TYPE: DNA
<213> ORGANISM: Artificial sequence
<220> FEATURE:
<223> OTHER INFORMATION: VH domain nucleic acid sequence

<400> SEQUENCE: 8
caggtccagc tggtacagtc tggggctgag gtgaagaagc ctggggcctc agtgaaggtc      60
tcctgcaagg tttccggata caccctcact gaattatcca tgcactgggt gcgacaggct     120
cctggaaaag gcttgagtg gatgggaggt tttgatcctg aagatggtga acaatctac      180 gcacagaagt tccagggcag agtcaccatg accgaggaca catctacaga cacagcctac     240
atggagctga gcagcctggg atctgaggac acggccgtgt attactgtgc gagacgcgtt     300
tgggggagtt atcgccccaa tgatgctttt gatatctggg gccaaggaac cctggtcacc     360
gtctcctca                                                             369

<210> SEQ ID NO 9
<211> LENGTH: 108
<212> TYPE: PRT
<213> ORGANISM: Artificial sequence
<220> FEATURE:
<223> OTHER INFORMATION: VL domain amino acid sequence

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
            20                  25                  30

Val Asn Trp Tyr Gln Gln Lys Pro Gly Lys Ala Pro Asn Leu Leu Met
        35                  40                  45

Phe Ala Ala Ser Thr Ser Gln Ser Gly Val Pro Ser Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Ser Pro Pro Tyr
                85                  90                  95

Thr Phe Gly Gln Gly Thr Lys Val Glu Ile Lys Arg
            100                 105

<210> SEQ ID NO 10
<211> LENGTH: 324
<212> TYPE: DNA
<213> ORGANISM: Artificial sequence
<220> FEATURE:
<223> OTHER INFORMATION: VL domain nucleic acid sequence

<400> SEQUENCE: 10
gacatccaga tgacccagtc tccatcctcc ctgtctgcat ctgtaggcga cagagtcacc      60
atcacttgcc gggcaagtca gagcataagc gactatgtaa actggtatca gcagaaacca     120
gggaaagccc ccaacctcct gatgtttgct gcatccactt cgcaaagtgg ggtcccgtca     180
aggttcactg gcagcggatc tgggacagat ttcactctca ccatcagcag tctgcaacct     240
gaagattttg caacttactt ctgtcaacag agttacagtc cgccctacac ttttggccag     300
gggaccaagg tggagatcaa acgt                                            324

<210> SEQ ID NO 11
<211> LENGTH: 283
<212> TYPE: PRT
<213> ORGANISM: Artificial sequence
<220> FEATURE:
<223> OTHER INFORMATION: 114_3H1 scFv, Lead antibody sequence

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Gly Ser Glu Asp Thr Ala Val Tyr Tyr Cys
                85                  90                  95

Ala Arg Arg Val Trp Gly Ser Tyr Arg Pro Asn Asp Ala Phe Asp Ile
            100                 105                 110

Trp Gly Gln Gly Thr Leu Val Thr Val Ser Ser Leu Glu Gly Gly Gly
    115                 120                 125

Gly Ser Gly Gly Gly Gly Ser Gly Gly Gly Ala Ser Asp Ile Gln Met
        130                 135                 140

Thr Gln Ser Pro Ser Ser Leu Ser Ala Ser Val Gly Asp Arg Val Thr
145                 150                 155                 160

Ile Thr Cys Arg Ala Ser Gln Ser Ile Ser Asp Tyr Val Asn Trp Tyr
                165                 170                 175

Gln Gln Lys Pro Gly Lys Ala Pro Asn Leu Leu Met Phe Ala Ala Ser

-continued

```
                180                 185                 190
Thr Ser Gln Ser Gly Val Pro Ser Arg Phe Thr Gly Ser Gly Ser Gly
            195                 200                 205

Thr Asp Phe Thr Leu Thr Ile Ser Ser Leu Gln Pro Glu Asp Phe Ala
        210                 215                 220

Thr Tyr Phe Cys Gln Gln Ser Tyr Ser Pro Pro Tyr Thr Phe Gly Gln
225                 230                 235                 240

Gly Thr Lys Val Glu Ile Lys Arg Ala Ala Ala Ser Ala His His His
                245                 250                 255

His His His Lys Leu Asp Tyr Lys Asp His Asp Gly Asp Tyr Lys Asp
            260                 265                 270

His Asp Ile Asp Tyr Lys Asp Asp Asp Lys
        275                 280

<210> SEQ ID NO 12
<211> LENGTH: 5
<212> TYPE: PRT
<213> ORGANISM: Artificial sequence
<220> FEATURE:
<223> OTHER INFORMATION: CDR-H1 amino acid sequence 113_1H12

<400> SEQUENCE: 12

Asn Tyr Gly Ile Ser
1               5

<210> SEQ ID NO 13
<211> LENGTH: 17
<212> TYPE: PRT
<213> ORGANISM: Artificial sequence
<220> FEATURE:
<223> OTHER INFORMATION: CDR-H2 amino acid sequence 113_1H12

<400> SEQUENCE: 13

Trp Ile Ser Ala Tyr Asn Gly Asn Thr Asn Tyr Ala Gln Lys Leu Gln
1               5                   10                  15

Gly

<210> SEQ ID NO 14
<211> LENGTH: 12
<212> TYPE: PRT
<213> ORGANISM: Artificial sequence
<220> FEATURE:
<223> OTHER INFORMATION: CDR-H3 amino acid sequence 113_1H12

<400> SEQUENCE: 14

Ala Gly Gly Val Tyr Tyr Asp Tyr Phe Thr Asp Tyr
1               5                   10

<210> SEQ ID NO 15
<211> LENGTH: 13
<212> TYPE: PRT
<213> ORGANISM: Artificial sequence
<220> FEATURE:
<223> OTHER INFORMATION: CDR-L1 amino acid sequence 113_1H12

<400> SEQUENCE: 15

Ser Gly Ser Arg Ser Asn Ile Gly Ser Asn Ser Val Asn
1               5                   10

<210> SEQ ID NO 16
<211> LENGTH: 7
<212> TYPE: PRT
<213> ORGANISM: Artificial sequence
```

```
<220> FEATURE:
<223> OTHER INFORMATION: CDR-L2 amino acid sequence 113_1H12

<400> SEQUENCE: 16

Asn Asn Asp Glu Arg Pro Ser
1               5

<210> SEQ ID NO 17
<211> LENGTH: 12
<212> TYPE: PRT
<213> ORGANISM: Artificial sequence
<220> FEATURE:
<223> OTHER INFORMATION: CDR-L3 amino acid sequence 113_1H12

<400> SEQUENCE: 17

Ala Ala Trp Asp Asp Ser Leu Asn Val Gly Glu Leu
1               5                   10

<210> SEQ ID NO 18
<211> LENGTH: 121
<212> TYPE: PRT
<213> ORGANISM: Artificial sequence
<220> FEATURE:
<223> OTHER INFORMATION: VH domain amino acid sequence

<400> SEQUENCE: 18

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Asn Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Gly Gly Val Tyr Tyr Asp Tyr Phe Thr Asp Tyr Trp Gly
            100                 105                 110

Gln Gly Thr Met Val Thr Val Ser Ser
        115                 120

<210> SEQ ID NO 19
<211> LENGTH: 369
<212> TYPE: DNA
<213> ORGANISM: Artificial sequence
<220> FEATURE:
<223> OTHER INFORMATION: VH domain nucleic acid sequence

<400> SEQUENCE: 19
atggccgagg tgcagctggt gcagtctgga gctgaggtga agaagcctgg ggcctcagtg      60
aaggtctcct gcaagacttc tggttacacc tttaccaact atggtatcag ctgggtgcga    120
caggcccctg gacaagggct tgagtggatg ggatggatca gcgcttacaa tggtaacacg    180
aactatgcac agaagctcca gggcagagtc accatgacca cagacacatc cacgagcaca    240
gcctacatgg agctgaggag cctgagatct gacgacacgg ccgtgtatta ctgcgcgaga    300
gccggcggag tctattacga ttatttcacg gactactggg gccaggggac aatggtcacc    360
gtctcttca                                                            369
```

<210> SEQ ID NO 20
<211> LENGTH: 112
<212> TYPE: PRT
<213> ORGANISM: Artificial sequence
<220> FEATURE:
<223> OTHER INFORMATION: VL domain amino acid sequence

<400> SEQUENCE: 20

```
Gln Ser Glu Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Ser Val Asn Trp Tyr Gln Gln Leu Pro Gly Thr Ala Pro Lys Leu Leu
        35                  40                  45

Ile Tyr Asn Asn Asp Glu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ala Trp Asp Asp Ser Leu
                85                  90                  95

Asn Val Gly Glu Leu Phe Gly Gly Gly Thr Lys Leu Thr Val Leu Gly
            100                 105                 110
```

<210> SEQ ID NO 21
<211> LENGTH: 336
<212> TYPE: DNA
<213> ORGANISM: Artificial sequence
<220> FEATURE:
<223> OTHER INFORMATION: VL domain nucleic acid sequence

<400> SEQUENCE: 21

```
cagtctgagc tgactcagcc accctcagcg tctgggaccc ccgggcagag ggtcaccatc      60
tcttgttctg gaagccgctc caacatcgga agtaattctg taaactggta ccagcagctc     120
ccaggaacgg cccccaaact cctcatttat aataatgatg agcggccctc aggggtccct     180
gaccgattct ctggctccaa gtctggcacc tcagcctccc tggccatcag tgggctccag     240
tctgaggatg aggctgatta tttctgtgca gcatgggatg acagcctgaa tgtcggggag     300
ctattcggcg gagggaccaa gctgaccgtc ctaggt                               336
```

<210> SEQ ID NO 22
<211> LENGTH: 285
<212> TYPE: PRT
<213> ORGANISM: Artificial sequence
<220> FEATURE:
<223> OTHER INFORMATION: 113_1H12 scFv, Lead antibody sequence

<400> SEQUENCE: 22

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
```

```
                        85                  90                  95
Ala Arg Ala Gly Gly Val Tyr Tyr Asp Tyr Phe Thr Asp Tyr Trp Gly
                100                 105                 110

Gln Gly Thr Met Val Thr Val Ser Ser Leu Glu Gly Gly Gly Gly Ser
            115                 120                 125

Gly Gly Gly Gly Ser Gly Gly Ala Ser Gln Ser Glu Leu Thr Gln
        130                 135                 140

Pro Pro Ser Ala Ser Gly Thr Pro Gly Gln Arg Val Thr Ile Ser Cys
145                 150                 155                 160

Ser Gly Ser Arg Ser Asn Ile Gly Ser Asn Ser Val Asn Trp Tyr Gln
                165                 170                 175

Gln Leu Pro Gly Thr Ala Pro Lys Leu Leu Ile Tyr Asn Asn Asp Glu
            180                 185                 190

Arg Pro Ser Gly Val Pro Asp Arg Phe Ser Gly Ser Lys Ser Gly Thr
            195                 200                 205

Ser Ala Ser Leu Ala Ile Ser Gly Leu Gln Ser Glu Asp Glu Ala Asp
210                 215                 220

Tyr Phe Cys Ala Ala Trp Asp Ser Leu Asn Val Gly Glu Leu Phe
225                 230                 235                 240

Gly Gly Gly Thr Lys Leu Thr Val Leu Gly Ala Ala Ser Ala His
                245                 250                 255

His His His His Lys Leu Asp Tyr Lys Asp His Asp Gly Asp Tyr
            260                 265                 270

Lys Asp His Asp Ile Asp Tyr Lys Asp Asp Asp Lys
            275                 280                 285

<210> SEQ ID NO 23
<211> LENGTH: 89
<212> TYPE: PRT
<213> ORGANISM: Homo sapiens

<400> SEQUENCE: 23

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 24
<211> LENGTH: 68
<212> TYPE: PRT
<213> ORGANISM: Homo sapiens

<400> SEQUENCE: 24

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
```

```
                35                  40                  45

Val Cys Ile Asp Pro Lys Leu Lys Trp Ile Gln Glu Tyr Leu Glu Lys
    50                  55                  60

Ala Leu Asn Lys
65
```

<210> SEQ ID NO 25
<211> LENGTH: 81
<212> TYPE: PRT
<213> ORGANISM: Artificial sequence
<220> FEATURE:
<223> OTHER INFORMATION: Recombinant "wild-type" CXCL12 expressed in
      E.coli for epitope mapping (including His tag and linker)

<400> SEQUENCE: 25

```
Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
    50                  55                  60

Ala Leu Asn Lys Ala Ala Ala Ser Ala His His His His His His Lys
65                  70                  75                  80

Leu
```

<210> SEQ ID NO 26
<211> LENGTH: 14
<212> TYPE: PRT
<213> ORGANISM: Artificial sequence
<220> FEATURE:
<223> OTHER INFORMATION: VH CDR3

<400> SEQUENCE: 26

```
Leu Ile Ser Gly Ser Tyr Arg Leu Glu Asp Tyr Phe Asp His
1               5                   10
```

<210> SEQ ID NO 27
<211> LENGTH: 20
<212> TYPE: PRT
<213> ORGANISM: Artificial sequence
<220> FEATURE:
<223> OTHER INFORMATION: VH CDR3

<400> SEQUENCE: 27

```
Glu Ala Ser Asp Pro Arg Tyr Tyr Tyr Asp Ser Ser Gly Tyr Tyr Tyr
1               5                   10                  15

Gly Met Asp Val
            20
```

<210> SEQ ID NO 28
<211> LENGTH: 10
<212> TYPE: PRT
<213> ORGANISM: Artificial sequence
<220> FEATURE:
<223> OTHER INFORMATION: VH CDR3

<400> SEQUENCE: 28

```
Asp Tyr Asn Asp Trp Gly Ala Phe Glu Leu
1               5                   10
```

```
<210> SEQ ID NO 29
<211> LENGTH: 21
<212> TYPE: PRT
<213> ORGANISM: Artificial sequence
<220> FEATURE:
<223> OTHER INFORMATION: VH CDR3

<400> SEQUENCE: 29

Glu Gly Tyr Asp Ser Ser Gly Tyr Gly Ala Arg Pro Arg Tyr Tyr
1               5                   10                  15

Tyr Gly Met Asp Val
            20

<210> SEQ ID NO 30
<211> LENGTH: 15
<212> TYPE: PRT
<213> ORGANISM: Artificial sequence
<220> FEATURE:
<223> OTHER INFORMATION: VH CDR3

<400> SEQUENCE: 30

Asp Ser Leu Asp Gly Asn Gly Ser Trp Asp Asp Ala Phe Asp Ile
1               5                   10                  15

<210> SEQ ID NO 31
<211> LENGTH: 24
<212> TYPE: PRT
<213> ORGANISM: Artificial sequence
<220> FEATURE:
<223> OTHER INFORMATION: VH CDR3

<400> SEQUENCE: 31

Gly Ser Ala Tyr Tyr Tyr Gly Ser Gly Ser Tyr Tyr Lys Ala Pro Tyr
1               5                   10                  15

Tyr Tyr Tyr Tyr Gly Met Asp Val
            20

<210> SEQ ID NO 32
<211> LENGTH: 8
<212> TYPE: PRT
<213> ORGANISM: Artificial sequence
<220> FEATURE:
<223> OTHER INFORMATION: VH CDR3

<400> SEQUENCE: 32

Gly Met Gly Tyr Gly Met Asp Leu
1               5

<210> SEQ ID NO 33
<211> LENGTH: 13
<212> TYPE: PRT
<213> ORGANISM: Artificial sequence
<220> FEATURE:
<223> OTHER INFORMATION: VH CDR3

<400> SEQUENCE: 33

Glu Gly Gly Asp Pro Thr Thr Pro Thr Thr Thr Thr Val
1               5                   10

<210> SEQ ID NO 34
<211> LENGTH: 9
<212> TYPE: PRT
<213> ORGANISM: Artificial sequence
<220> FEATURE:
<223> OTHER INFORMATION: VH CDR3

<400> SEQUENCE: 34
```

Asp Asp Ser Thr Ala Asp Leu Asp Tyr
1               5

<210> SEQ ID NO 35
<211> LENGTH: 10
<212> TYPE: PRT
<213> ORGANISM: Artificial sequence
<220> FEATURE:
<223> OTHER INFORMATION: VL CDR3

<400> SEQUENCE: 35

Gln Ala Trp Asp Ser Ser Thr Gly Tyr Val
1               5                   10

<210> SEQ ID NO 36
<211> LENGTH: 9
<212> TYPE: PRT
<213> ORGANISM: Artificial sequence
<220> FEATURE:
<223> OTHER INFORMATION: VL CDR3

<400> SEQUENCE: 36

Gln Gln Tyr Asp Asn Leu Pro Leu Thr
1               5

<210> SEQ ID NO 37
<211> LENGTH: 9
<212> TYPE: PRT
<213> ORGANISM: Artificial sequence
<220> FEATURE:
<223> OTHER INFORMATION: VL CDR3

<400> SEQUENCE: 37

Gln Lys Tyr Asn Ser Ala Pro Arg Thr
1               5

<210> SEQ ID NO 38
<211> LENGTH: 9
<212> TYPE: PRT
<213> ORGANISM: Artificial sequence
<220> FEATURE:
<223> OTHER INFORMATION: VL CDR3

<400> SEQUENCE: 38

Val Gln Gly Thr His Trp Pro Trp Thr
1               5

<210> SEQ ID NO 39
<211> LENGTH: 9
<212> TYPE: PRT
<213> ORGANISM: Artificial sequence
<220> FEATURE:
<223> OTHER INFORMATION: VL CDR3

<400> SEQUENCE: 39

Gln Gln Ser Tyr Asn Thr Pro Arg Thr
1               5

<210> SEQ ID NO 40
<211> LENGTH: 9
<212> TYPE: PRT
<213> ORGANISM: Artificial sequence
<220> FEATURE:
<223> OTHER INFORMATION: VL CDR3

<400> SEQUENCE: 40

```
Val Gln Gly Thr His Trp Pro Trp Thr
1               5

<210> SEQ ID NO 41
<211> LENGTH: 9
<212> TYPE: PRT
<213> ORGANISM: Artificial sequence
<220> FEATURE:
<223> OTHER INFORMATION: VL CDR3

<400> SEQUENCE: 41

Gln Ser Tyr Asp Ser Ser Asn Gln Val
1               5

<210> SEQ ID NO 42
<211> LENGTH: 9
<212> TYPE: PRT
<213> ORGANISM: Artificial sequence
<220> FEATURE:
<223> OTHER INFORMATION: VL CDR3

<400> SEQUENCE: 42

Gln Gln Tyr Asp Asn Leu Pro Tyr Thr
1               5

<210> SEQ ID NO 43
<211> LENGTH: 10
<212> TYPE: PRT
<213> ORGANISM: Artificial sequence
<220> FEATURE:
<223> OTHER INFORMATION: VL CDR3

<400> SEQUENCE: 43

Cys Ser Tyr Ala Gly Pro Phe Thr Val Ile
1               5                   10

<210> SEQ ID NO 44
<211> LENGTH: 12
<212> TYPE: PRT
<213> ORGANISM: Artificial sequence
<220> FEATURE:
<223> OTHER INFORMATION: VL CDR3

<400> SEQUENCE: 44

Ala Ala Trp Asp Asp Ser Leu Ser Gly Pro Tyr Val
1               5                   10

<210> SEQ ID NO 45
<211> LENGTH: 122
<212> TYPE: PRT
<213> ORGANISM: Homo sapiens

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Lys Leu
                20                  25                  30

Ser Val His Trp Val Arg Gln Ala Pro Gly Lys Gly Leu Glu Trp Met
            35                  40                  45

Gly Ser Phe Asp Pro Glu Asp Gly Glu Thr Ile Tyr Ser Gln Arg Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
```

```
                    85                  90                  95
Ala Thr Glu Gly Gln Trp Leu Val Ala Tyr Tyr Gly Met Asp Val Trp
                100                 105                 110

Gly Gln Gly Thr Met Val Thr Val Ser Ser
        115                 120

<210> SEQ ID NO 46
<211> LENGTH: 122
<212> TYPE: PRT
<213> ORGANISM: Homo sapiens

<400> SEQUENCE: 46

Glu Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Lys Leu
            20                  25                  30

Ser Val His Trp Val Arg Gln Ala Pro Gly Lys Gly Leu Glu Trp Met
        35                  40                  45

Gly Ser Phe Asp Pro Glu Asp Gly Glu Thr Ile Tyr Ser Gln Arg Phe
    50                  55                  60

Gln Gly Arg Val Thr Met Thr Glu Asp Thr Ser Thr Asp Thr Ala Tyr
65                  70                  75                  80

Met Glu Leu Thr Ser Leu Arg Ser Glu Asp Thr Ala Val Tyr Tyr Cys
                85                  90                  95

Ala Thr Glu Gly Gln Trp Leu Val Ala Tyr Tyr Gly Met Asp Val Trp
                100                 105                 110

Gly Gln Gly Thr Thr Val Thr Val Ser Ser
        115                 120

<210> SEQ ID NO 47
<211> LENGTH: 124
<212> TYPE: PRT
<213> ORGANISM: Homo sapiens

<400> SEQUENCE: 47

Glu Val Gln Leu Val Glu Ser Gly Arg Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Met Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Thr Gly Pro Tyr Tyr Tyr Asp Tyr Tyr Gly Met Asp
                100                 105                 110

Val Trp Gly Gln Gly Thr Thr Val Thr Val Ser Ser
        115                 120

<210> SEQ ID NO 48
<211> LENGTH: 124
<212> TYPE: PRT
<213> ORGANISM: Homo sapiens

<400> SEQUENCE: 48
```

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Met Asn Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Leu Thr Gly Pro Tyr Tyr Tyr Asp Tyr Tyr Gly Met Asp
                100                 105                 110

Val Trp Gly Gln Gly Thr Thr Val Thr Val Ser Ser
            115                 120

<210> SEQ ID NO 49
<211> LENGTH: 107
<212> TYPE: PRT
<213> ORGANISM: Homo sapiens

<400> SEQUENCE: 49

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
            85                  90                  95

Thr Phe Gly Gly Gly Thr Lys Val Glu Ile Lys
                100                 105

<210> SEQ ID NO 50
<211> LENGTH: 107
<212> TYPE: PRT
<213> ORGANISM: Homo sapiens

<400> SEQUENCE: 50

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
            85                  90                  95

-continued

Thr Phe Gly Gly Gly Thr Lys Val Glu Ile Lys
            100                 105

<210> SEQ ID NO 51
<211> LENGTH: 107
<212> TYPE: PRT
<213> ORGANISM: Homo sapiens

<400> SEQUENCE: 51

Ala Ile Arg Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Thr Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Gln Gly Thr Lys Val Glu Ile Lys
            100                 105

<210> SEQ ID NO 52
<211> LENGTH: 107
<212> TYPE: PRT
<213> ORGANISM: Homo sapiens

<400> SEQUENCE: 52

Asp Ile Gln Met Ile Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Gln Gly Thr Lys Val Glu Ile Lys
            100                 105

<210> SEQ ID NO 53
<211> LENGTH: 17
<212> TYPE: PRT
<213> ORGANISM: Artificial Sequence
<220> FEATURE:
<223> OTHER INFORMATION: VH CDR3

<400> SEQUENCE: 53

Asp Ser Leu Asp Gly Asn Gly Ser Gly Ser Trp Asp Asp Ala Phe Asp
1               5                   10                  15

Ile